(12) United States Patent
Brubacher

(10) Patent No.: US 9,644,229 B2
(45) Date of Patent: May 9, 2017

(54) MICROORGANISM EVALUATION SYSTEM

(71) Applicant: SoBru Solutions, Inc., Fullerton, CA (US)

(72) Inventor: John Miles Brubacher, La Mirada, CA (US)

(73) Assignee: SOBRU SOLUTIONS, INC., Fullerton, CA (US)

( * ) Notice: Subject to any disclaimer, the term of this patent is extended or adjusted under 35 U.S.C. 154(b) by 0 days.

(21) Appl. No.: 14/408,562

(22) PCT Filed: Jun. 18, 2013

(86) PCT No.: PCT/US2013/046334
§ 371 (c)(1),
(2) Date: Dec. 16, 2014

(87) PCT Pub. No.: WO2013/192187
PCT Pub. Date: Dec. 27, 2013

(65) Prior Publication Data
US 2015/0167045 A1 Jun. 18, 2015

Related U.S. Application Data

(60) Provisional application No. 61/661,011, filed on Jun. 18, 2012.

(51) Int. Cl.
*C12M 1/00* (2006.01)
*C12Q 1/04* (2006.01)
(Continued)

(52) U.S. Cl.
CPC ............. *C12Q 1/04* (2013.01); *G01N 15/147* (2013.01); *B01L 3/502* (2013.01);
(Continued)

(58) Field of Classification Search
CPC ....... B01L 3/502715; B01L 2200/0652; G01N 15/147; C12C 1/04
(Continued)

(56) References Cited

U.S. PATENT DOCUMENTS 4,380,392 A 4/1983 Karabegov et al.
4,824,449 A 4/1989 Majoros
(Continued)

FOREIGN PATENT DOCUMENTS

CN 101750435 A 6/2010
EP 0530490 A1 3/1992
(Continued)

OTHER PUBLICATIONS

International Search Report, PCT/US13/46334, dated Nov. 1, 2013.
(Continued)

*Primary Examiner* — Nathan Bowers
(74) *Attorney, Agent, or Firm* — Lodestone Legal Group; Jeromye V. Sartain

(57) ABSTRACT

A microorganism evaluation system for analyzing microorganisms within a fluid flow, comprising a microorganism stimulation section comprising a means for inducing a motive response in a living microorganism within the fluid flow passing through the microorganism stimulation section, and a viewing section in fluid communication with the microorganism stimulation section, the viewing section comprising a body having formed therein a body cavity defining a viewing port visible through a cavity first opening formed in the body so as to be in communication with the body cavity, the viewing section further comprising an optical system mounted relative to the body for viewing the fluid flow within the viewing port through the cavity first
(Continued)

opening, whereby image data relating to the fluid flow and microorganisms therein is acquired via the optical system for analysis.

23 Claims, 16 Drawing Sheets

(51) Int. Cl.
    *A01B 1/00*     (2006.01)
    *G01N 15/14*     (2006.01)
    *C12M 1/34*     (2006.01)
    *G01N 15/00*     (2006.01)
    *G01N 15/10*     (2006.01)
    *B01L 3/00*     (2006.01)

(52) U.S. Cl.
CPC . *B01L 2200/026* (2013.01); *B01L 2200/0636* (2013.01); *B01L 2200/0652* (2013.01); *B01L 2300/023* (2013.01); *C12M 41/36* (2013.01); *G01N 2015/0065* (2013.01); *G01N 2015/1075* (2013.01)

(58) Field of Classification Search
    IPC .................................................. B01L 3/502715
    See application file for complete search history.

(56) References Cited

U.S. PATENT DOCUMENTS

| | | | |
|---|---|---|---|
| 6,498,862 | B1 | 12/2002 | Pierson et al. |
| 7,901,937 | B2 * | 3/2011 | Srienc .................... C12M 47/04 435/288.7 |
| 7,999,937 | B1 * | 8/2011 | Srivastava ........ B01L 3/502746 356/338 |
| 8,153,950 | B2 | 4/2012 | Kiesel et al. |
| 2002/0094584 | A1 | 7/2002 | Shieh et al. |
| 2003/0175687 | A1 | 9/2003 | Tippet |
| 2004/0136870 | A1 | 7/2004 | Kochy et al. |
| 2006/0210962 | A1 | 9/2006 | Imaizumi et al. |
| 2006/0257993 | A1 * | 11/2006 | McDevitt .......... B01L 3/502715 435/287.2 |
| 2009/0093045 | A1 | 4/2009 | Takenaka et al. |
| 2009/0162887 | A1 | 6/2009 | Kaduchak et al. |
| 2010/0041122 | A1 | 2/2010 | Ragsdale |
| 2010/0116647 | A1 | 5/2010 | Kornmuller et al. |
| 2010/0157291 | A1 | 6/2010 | Kiesel et al. |
| 2010/0273208 | A1 | 10/2010 | Takenaka et al. |
| 2011/0096327 | A1 * | 4/2011 | Papautsky .......... B01D 21/0087 356/335 |
| 2012/0115723 | A1 | 5/2012 | Stimson et al. |
| 2012/0214224 | A1 * | 8/2012 | Chan .................... B01F 5/0647 435/287.2 |

FOREIGN PATENT DOCUMENTS

| | | |
|---|---|---|
| EP | 2026057 A2 | 2/2009 |
| JP | 2005106454 A1 | 3/2008 |
| JP | 2012020218 A | 2/2012 |
| WO | 2008130977 A2 | 10/2008 |

OTHER PUBLICATIONS

Malits et al. "Effect of turbulence and viruses on prokaryotic cell size, production and diversity" Aquatic Microbial Ecology 54, No. 3 (2009): 243-254. Abstract.

European Search Report, EP 13807665, dated Jan. 5, 2016.

* cited by examiner

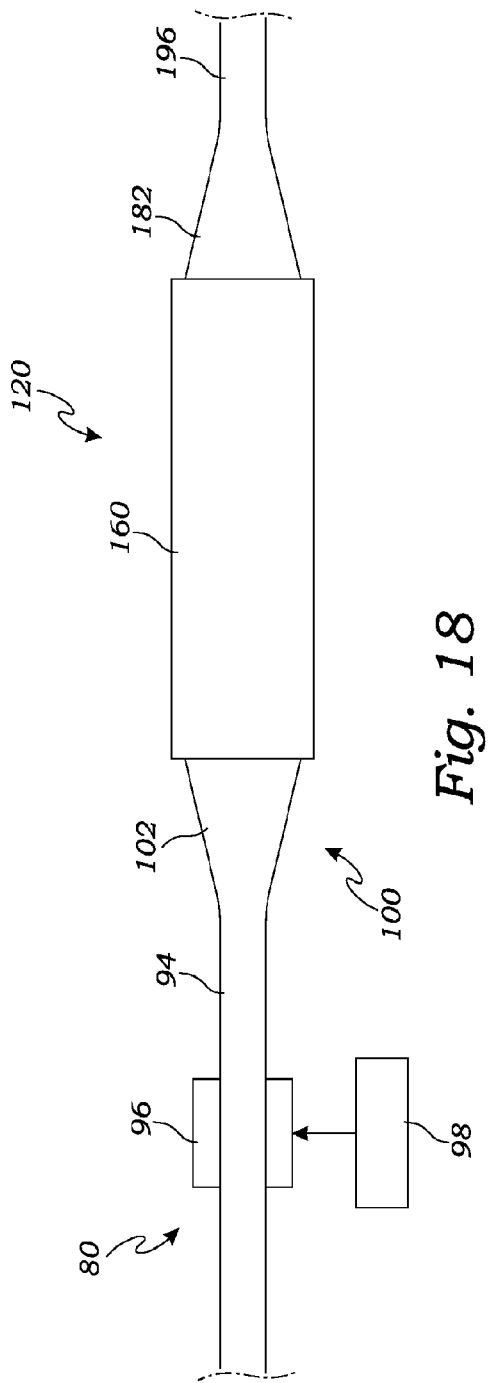
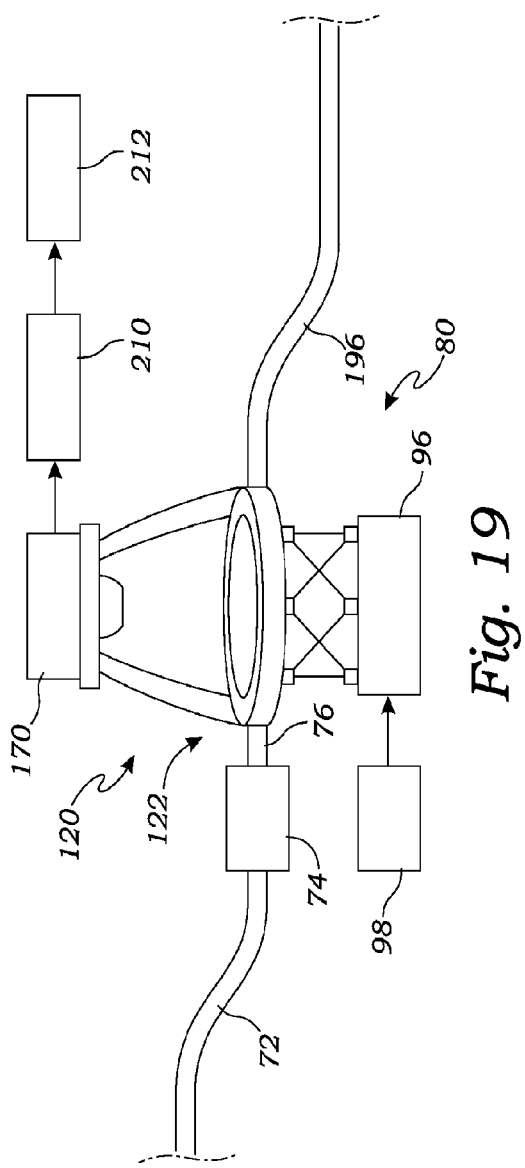
Fig. 18
Fig. 19

MICROORGANISM EVALUATION SYSTEM

RELATED APPLICATIONS

This application claims priority to and is entitled to the filing date of U.S. Provisional application Ser. No. 61/661,011 filed Jun. 18, 2012, and entitled "Microorganism Evaluation System." The contents of the aforementioned application are incorporated herein by reference.

INCORPORATION BY REFERENCE

Applicant(s) hereby incorporate herein by reference any and all patents and published patent applications cited or referred to in this application.

TECHNICAL FIELD

Aspects of this invention relate generally to testing systems, and more particularly to evaluation systems for determining whether microorganisms are living.

BACKGROUND ART

By way of background, a number of industries are affected by regulations relating to water treatment, such as ballast water treatment systems ("BWTS") on ships and the like. Such regulations require that microorganisms be effectively treated (killed) by the BWTS before such water is returned to the ocean or other body of water. Generally speaking, Zooplankton in the size range of approximately 10 to 50 microns is an "indicator" microorganism used to determine the effectiveness of treatment. To date, monitoring of the effectiveness of such BWTS has largely been handled through samples submitted to a lab, there most often involving human examination under a microscope. Such approaches to compliance assessment have numerous shortcomings in terms of accuracy, speed, and cost. Similarly, flow cytometry systems, though offering relatively higher throughput, are also lacking in terms of viability determination (determinations regarding whether an organism is living) and portability for field or deployed uses.

The following art defines the present state of this field:

International Pub. No. JP WO20051064545 dated Mar. 21, 2008 is directed to subject matter teaching that to be viable in the antigen by specifically labeled, as among a viable microorganisms can be detected rapidly in a short time, the reliability of inspection and detection method can also be guaranteed. Such as an antigen, *Escherichia coli*, viable to be examined in the antigen (target bacteria 12) enzymatic decomposition by the sign material 13 is brought into action after generating a labeled antigen 14, specifically to subject the specific coupling in a stationary phase is formed by fixing an antibody, an antigen labeled 14 thereof to and captured.

U.S. Patent Application Pub. No. US 2009/0162887 to Kaduchak et al. dated Jun. 25, 2009, is directed to a method and apparatus for acoustically manipulating one or more particles.

U.S. Patent Application Pub. No. US 2010/0041122 to Ragsdale dated Feb. 18, 2010, is directed to membrane-encased structures such as biological cells, liposomes, and vesicles, conveyed through one or more channels in a rotating disk for individual exposure to optical elements or to electrodes, for purposes of transfection or flow cytometry. The rotation of the disk serves either to provide centrifugal force to urge the cells against one wall of the channel and in certain embodiments to move the cells through the channels, or to draw cells at preselected times or intervals into the exposure zone, or all three.

U.S. Patent Application Pub. No. US 2010/0116647 to Kornmuller et al. dated May 13, 2010, is directed to a water treatment plant, in particular ballast water treatment plant, for removing sediments and/or removing and/or destroying living organisms, which has at least one filter unit (B) and at least one disinfection unit (C), wherein the plant has a detection unit (D) by means of which the number of living organisms of a presettable size per unit volume of water can be determined, and in that the plant has a control unit, by means of which the disinfection unit (C) can be controlled as a function of the number of living organisms which has been determined.

U.S. Patent Application Pub. No. US 2010/0157291 to Kiesel et al. dated Jun. 24, 2010, is directed to a method wherein sensors can be used to obtain encoded sensing results from objects that have nonuniform relative motion. A photosensor or impedance-based sensor, for example, can obtain sensing results from objects that have relative motion within a sensing region relative to the sensor, with the relative motion being, for example, periodically varying, randomly varying, chirp-varying, or modulated relative motion that completes at least one modulation cycle within the sensing region. Relative motion can be caused by varying objects' speed and/or direction or by controlling flow of fluid carrying objects, movement of a channel, movement of a support structure, movement of a sensor, and/or pattern movement. A fluidic implementation can include shaped channel wall parts and/or a displacement component causing time-varying lateral displacement. A support structure implementation can include a scanner device and a rotary device that respectively control scanning and rotating movement of a movable support structure or of a sensor.

Japanese Patent Application Pub. No. JP 2012020218 dated Feb. 2, 2012, is directed to a system wherein the liquid supplied to the ballast tank 103 in the sterilization of microorganisms hydrophyte for sterilization device 101 and 1, ballast water in the ballast tank 103 for sterilization device 102 and the second, first the liquid 1 sterilization treatment device 101 for supplying the chest 104 of the ballast from the ballast tank 103, 105 and connected to a water supply line, 2 sterilization treatment device 102 includes a first liquid containing sodium chloride, sodium hypochlorite by electrolysis in the electrolytic cell for generating the ballast water treatment system is provided.

U.S. Pat. No. 8,153,950 to Kiesel et al. dated Apr. 10, 2012, is directed to an encoder/sensor can obtain sensing results from objects in an encoding/sensing region; a trigger detector can respond to objects in a trigger detection region, providing respective trigger signals; and a relative motion component can cause relative motion of objects into the trigger detection region, from it into the encoding/sensing region, and within the encoding/sensing region. In response to an object's trigger signal, control circuitry can cause the encoder/sensor and/or the relative motion component to operate so that the encoder/sensor obtains sensing results indicating a time-varying waveform and processing circuitry can obtain data from the sensing results indicating a time-varying waveform. The time-varying waveform can include information resulting from the relative motion within the encoding/sensing region. The encoder/sensor and trigger detector can be implemented, for example, with discrete components or as sets of cells in a photosensing array on an integrated circuit.

U.S. Patent Application Pub. No. US 2012/0115723 to Stimson et al. dated May 10, 2012, is directed to a composition for treating waters, e.g. ballast water or injection water for oil recovery, to kill in-situ aquatic invasive species comprises at least one biocide capable of killing both animal and plant micro-organisms. The at least one biocide preferably comprises Brilliant Green, Gentian Violet, and/or erythrosine, and a wetting agent or detergent-like compound such as CTAB or CTAC. The invention also relates to a system for treating ballast water in situ comprising means for injecting a composition for treating ballast water; means for measuring the flow rate or amount of ballast water to be treated; means for controlling the dosing of the composition; and means for storing or receiving the composition. The invention also relates to a method of detecting viable aquatic organisms in ballast water in situ comprising detecting metabolism in viable micro-organisms in ballast water and, therefore, measuring the efficacy of any treatment.

The prior art described above teaches a viable specifically labeled antigen detection and detection device for detecting method, a particle analysis in an acoustic cytometer, a centrifugal force-based system for detection/treatment of membrane-encased structures, a ballast water treatment plant having filter, disinfection, instrumentation and control unit, a system for causing relative motion, a ballast water treatment system and ballast water treatment method, a system and method for obtaining sensing results and/or data in response to object detection, and a ballast water treatment system, but does not teach a means for imparting at least inertial stimulation to organisms within a fluid flow for the purpose of determining whether organisms are living based on detected responsive movement and/or motion of the organisms. Aspects of the present invention fulfill these needs and provide further related advantages as described in the following disclosure.

DISCLOSURE OF INVENTION

Aspects of the present invention teach certain benefits in construction and use which give rise to the exemplary advantages described below.

The present invention solves the problems described above by providing an evaluation system for determining whether a microorganism is living. The system provides, in the exemplary embodiment, a microorganism evaluation system for analyzing microorganisms within a fluid flow, comprising a microorganism stimulation section comprising a means for inducing a motive response in a living microorganism capable of such within the fluid flow passing through the microorganism stimulation section, and a viewing section in fluid communication with the microorganism stimulation section, the viewing section comprising a body having formed therein a body cavity defining a viewing port visible through a cavity first opening formed in the body so as to be in communication with the body cavity, the viewing section further comprising an optical system mounted relative to the body for viewing the fluid flow within the viewing port through the cavity first opening, whereby image data relating to the fluid flow and microorganisms therein is acquired via the optical system for analysis.

A primary objective inherent in the above described system and method of use is to provide advantages not taught by the prior art.

Another objective is to provide such a system wherein a flow normalizing section is in fluid communication between the microorganism stimulation section and the viewing section, the flow normalizing section comprising an inlet chute having a tapered inlet chute inner bore.

Yet another objective is to provide such a system wherein a sample pre-conditioning section is upstream of and in fluid communication with the microorganism stimulation section.

Other features and advantages of aspects of the present invention will become apparent from the following more detailed description, taken in conjunction with the accompanying drawings, which illustrate, by way of example, the principles of aspects of the invention.

BRIEF DESCRIPTION OF DRAWINGS

The accompanying drawings illustrate aspects of the present invention. In such drawings:

FIG. 18 is a partial schematic representation of an alternative exemplary microorganism evaluation system, in accordance with at least one embodiment;

FIG. 19 is a partial schematic representation of a further alternative exemplary microorganism evaluation system, in accordance with at least one embodiment.

Figure 1:
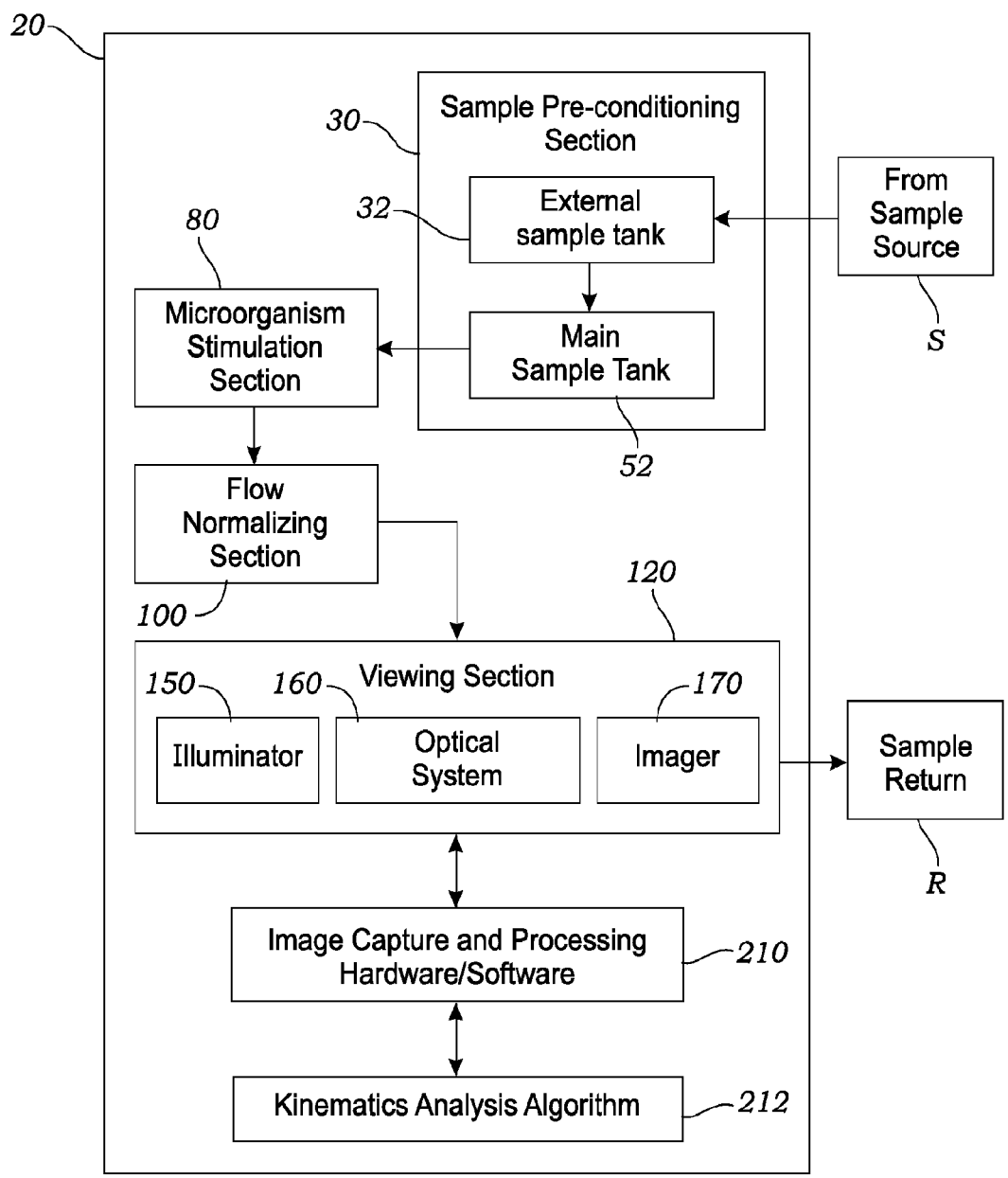
FIG. 1 is a block diagram illustrating an exemplary microorganism evaluation system, in accordance with at least one embodiment.

The above described drawing figures illustrate aspects of the invention in at least one of its exemplary embodiments, which are further defined in detail in the following description. Features, elements, and aspects of the invention that are referenced by the same numerals in different figures represent the same, equivalent, or similar features, elements, or aspects, in accordance with one or more embodiments.

MODES FOR CARRYING OUT THE INVENTION

The above described drawing figures illustrate aspects of the invention in at least one of its exemplary embodiments, which are further defined in detail in the following description.

In general, according to aspects of the present invention, batch or continuous real time monitoring is deployable within ballast water treatment systems and the like and provides further advantages over prior art test systems and approaches, the support of continuous real time monitoring being particularly advantageous for several applications. The subject invention, though again in the context of BWTS compliance testing, may be practiced in a wide array of contexts and so is not limited to the exemplary BWTS context (for example, monitoring invasive species migration in fresh and salt water bodies, bioterrorism, etc.). Thus, while "water" is discussed throughout as the sampled fluid, it is to be understood that the invention is not so limited and other fluids may be sampled as well, again depending on the context.

As an overview, and with reference to FIG. 1, the exemplary microorganism evaluation system 20 has four main hardware components or sections, which are discussed in turn below: (1) a sample pre-conditioning section 30; (2) a microorganism stimulation section 80; (3) a flow normalizing section 100; and (4) a viewing section 120. There are related tanks, tubes, flow controls and other aspects that facilitate the collection and processing of the water sample, which may be necessary in particular contexts but are nevertheless ancillary components that can be substituted for by other equivalent structure (e.g. pumps, etc.), and so are not the focus of the present invention. It will be appreciated by those skilled in the art that the exact configuration of the system and its four main sections may take a number of forms to suit particular applications without departing from the spirit and scope of the present invention. Accordingly, it will be further appreciated that the configurations of the system shown and described are exemplary and that the invention is not so limited. Moreover, once again, while "water" is discussed throughout as the sampled fluid, it is to be understood that the invention is not so limited and other fluids may be sampled as well, again depending on the context. Relatedly, it is assumed for these purposes that whatever fluid is sampled it contains microorganisms, some living and some dead, such as Zooplankton in the size range of approximately 10 to 50 microns, for example. It is further noted as a threshold matter that the present focus of the subject invention is in determining whether certain microorganisms are living, as again evidenced by a motive response of some kind, and not necessarily whether such an organism is "viable" in the sense that it is capable of living for an extended period, reproducing, etc., it being understood that all viable organisms are living but that not necessarily all living organisms are viable, though it will be appreciated that inherently the present invention will identify viable organisms as it does living ones.

With continued reference to FIG. 1, the block diagram shows the exemplary embodiment of the microorganism evaluation system 20 according to aspects of the present invention as generally comprising a sample pre-conditioning section 30 configured in fluid communication with a sample source S so as to receive and process a fluid sample and pass such sample along to a microorganism stimulation section 80 configured to agitate, excite, or otherwise stimulate one or more senses of any living microorganisms in the fluid sample. The sample pre-conditioning section 30 is shown as comprising an external sample tank 32 that receives the fluid flow from the sample source S and then passes such fluid on to a main sample tank 52 before then flowing to the microorganism stimulation section 80, though it will be appreciated that a variety of means for acquiring and passing along a fluid sample, static or dynamic and now known or later developed, may be employed without departing from the spirit and scope of the present invention, such that the two tanks in series are to be understood as merely exemplary of aspects of the invention. A flow normalizing section 100 is downstream of and in fluid communication with the microorganism stimulation section 80 for the purpose of slowing and/or rendering more laminar the fluid flow after it leaves the stimulation section 80, which may involve agitation of not just the organisms but the fluid itself. Downstream of and in fluid communication with the flow normalizing section 100 is a viewing section 120 configured for passing the flow therethrough and obtaining image data thereof. More particularly, in the exemplary embodiment, the viewing section 120 comprises an illuminator 150 for providing lighting to the viewing section 120, an optical system 160 for actually acquiring image data as would a camera or camera-like device, and an imager 170 for processing or manipulating the image data from the optical system 160. It will be appreciated that throughout when a "camera" is discussed is being the "optical system 160" or equipment that any such device, whether "off the shelf" or proprietary, may further include imaging capability, that is, the ability to capture and manipulate image data with sufficient frame rate and resolution, such that in fact the "optical system 160 and the imager 170 may be a single device in the form of a "camera" or the like. From the viewing section 120 the fluid flow proceeds to a sample return R. Further regarding the microorganism evaluation system 20, and the viewing section 120 specifically, there is shown a separate image capture and processing device 210 (hardware and software) in communication with the viewing section 120, which device 210 is configured for taking the image data from the imager 170 and further processing the data for analysis. The image capture and processing device 210 may be any computer or processor or computing or processing device now known or later developed and may be wired or wirelessly connected to the viewing section 120, or may be incorporated into the viewing section 120, and the imager 170 specifically, again for the purpose of acquiring and processing the image data obtained by the optical system 160. Moreover, the entire viewing section 120 may be a proprietary and/or unitary device or may be comprised of one or more "off the shelf" components operably connected and configured according to aspects of the present invention, such as, for example, employing a digital camera as the optical system 160 and outputting image data from such camera using its high-speed interface such as USB 2, HDMI, or other appropriate interface to a computer configured to operate as the imager 170 and image capture and processing device 210, or the viewing section 120 may be some combination thereof. Such computer may further have installed and run the kinematics analysis algorithm 212, or such algorithm 212 may be configured to operate on a separate computer or computing device. Ultimately, those skilled in the art will appreciate that the components of the viewing section 120, namely, the illuminator 150, the optical system 160, and the imager 170, and the related image capture and processing device 210 and kinematics analysis algorithm 212 may be configured in a variety of ways in one more devices without departing from the spirit and scope of the present invention, such that it is to be understood that the particular arrangement shown in FIG. 1 and elsewhere herein is merely illustrative of features and aspects of the present invention and non-limiting. Specifically, it will be appreciated that the image capture and processing device 210 and kinematics analysis algorithm 212 may be physically configured within the microorganism evaluation system 20 or not but are nevertheless components of the overall system 20 as represented by the block diagram of FIG. 1. Furthermore, any of the components of the system 20 may or may not be integral or packaged in a unitary way without departing from the spirit and scope of the invention.

Figure 2:
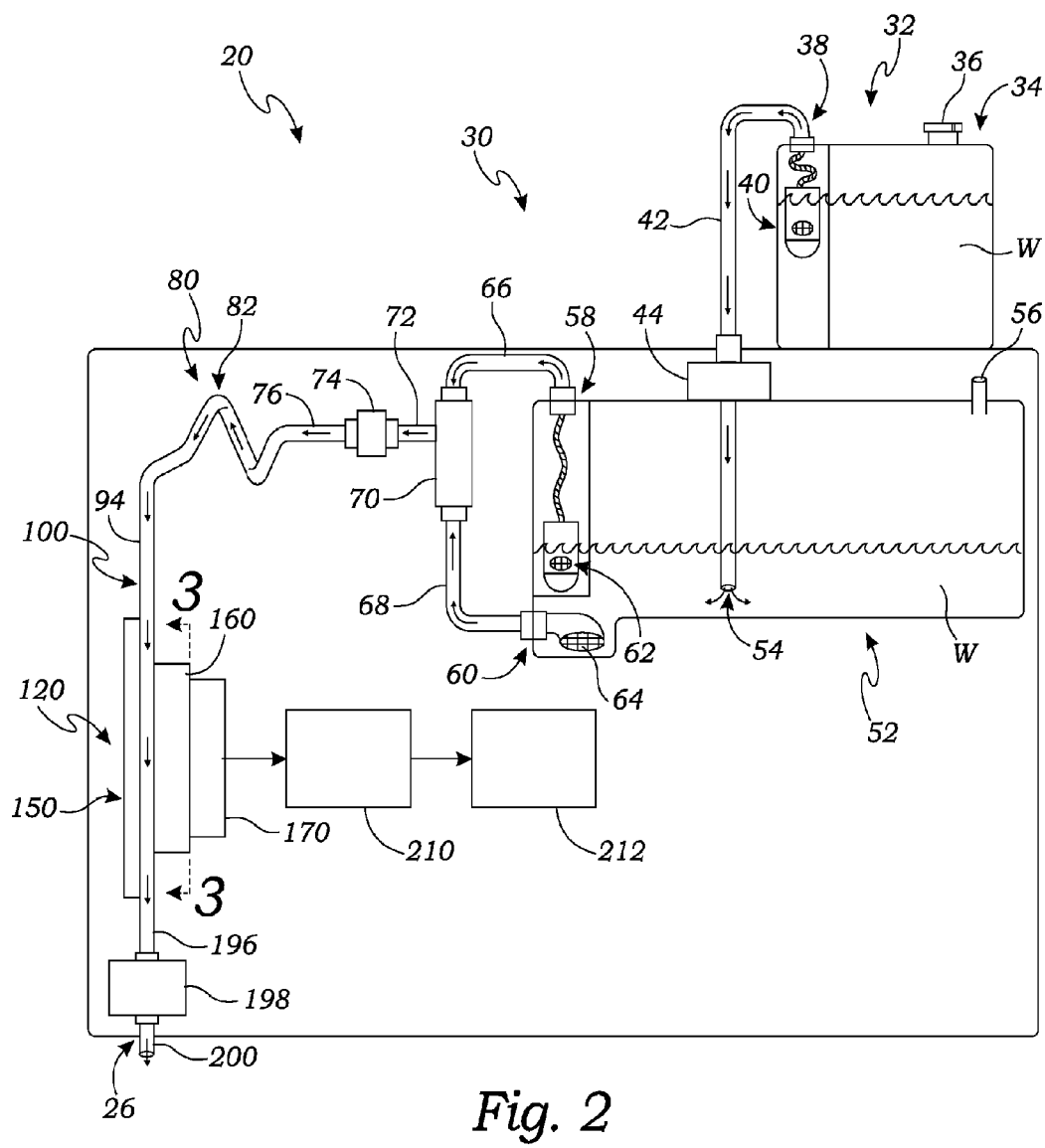
FIG. 2 is a schematic representation thereof, in accordance with at least one embodiment.

Turning now to FIG. 2, there is shown a schematic view, not to scale, of an exemplary embodiment of the microorganism evaluation system 20 according to aspects of the present invention as shown in the block diagram of FIG. 1. Going in sequence as a water sample would be processed through the system 20, and thus starting upstream of the stimulation section 80, there is again first the sample pre-conditioning section 30. This pre-conditioning section 30 can be implemented in different ways. For example, in real time continuous sampling applications the pre-conditioning function can be accomplished by utilizing the differing inertial characteristics of the particulates contained in the sampled fluid. Or, isokinetic or other techniques for sampling from a continuous flow now known or later developed may be substituted for the one or more tanks 32, 52 of the exemplary embodiment without departing from the spirit and scope of the present invention. Back to the discrete or static sample application, a removable external sample tank 32 is provided as a container into which a test sample is to be initially collected. While in FIG. 2 the initial external sample tank 32 is shown as being physically outside of the system, it is nevertheless part of the system 20, or the sample pre-conditioning section 30 specifically, as once again shown in the block diagram of FIG. 1. Such an external sample tank 32 may comprise a cap and vent 36 removably positioned in an inlet 34 and an external sample tank buoyant intake 40 configured with a filtered opening and a turbidity detection device (not shown) through which the sample fluid passes on its way to an outlet 38 of the external sample tank 32. By employing a buoyant sample intake 40, the intake is configured to resist dropping low enough in the tank 32 to pull in mud and other particulates that have settled to the bottom of the tank 32. The external sample tank 32 is thus configured as an initial sample fluid holding tank in which the sample is effectively pre-conditioned, particularly as to turbidity, before passing onto other portions of the microorganism evaluation system 20. Thus, the external sample tank 32 being removable facilitates the disposal of unwanted particulates such as mud deposits from turbid water and other inorganic or "dead" materials. A tank tubing 42 connects the outlet 38 of the external sample tank 32 to an inlet 54 of a main sample tank 52 installed within the system 20, the tubing 42 passing through a first opening 24 in the box or case or other such enclosure 22 in which the overall microorganism evaluation system 20 is installed and being coupled to the main sample tank 52 through a quick disconnect coupling 44 and a flow control 46 that cooperates with other aspects of the system's control sub-system in moving the fluid therethrough. Within the main sample tank 52, a down tube in the exemplary embodiment defining the inlet 54 is in fluid communication with the tubing 42 so as to effectively deliver the fluid from the external sample tank 32 to the bottom portion of the main sample tank 52, again for reasons related to turbidity and, more generally, consistent sample density during the sampling event. As with the external sample tank 32, the main sample tank 52 is also configured with a vent 56 and with a main sample tank buoyant intake 62 configured with a filtered opening through which the sample fluid passes on its way to an upper main sample tank first outlet 58. The main sample tank 52 is further configured with a lower main sample tank second outlet 60 having a main sample tank filtered intake 64 to allow fluid to pass therethrough as a means of essentially regulating the out-flow, in cooperation with the proportional flow valve 70 discussed below, such that the higher the column height of fluid in the main sample tank 52, the greater the tendency of fluid to pass out of the lower outlet 60, and vice versa. In other words, during the earlier period of the sampling event when the sample is at the greatest level in the tank 52, relatively less sample will flow from the buoyant intake 62 and relatively more from the lower fixed intake 64, and during the later period of the sampling event when the sample is at the lowest level in the tank 52, relatively more sample will flow through the buoyant intake 62 and relatively less sample will flow through the lower fixed intake 64. Moreover, since it is known that indicator organisms such as Zooplankton within a water sample will generally be at relatively greater concentrations at or near the surface and relatively lower concentrations at or near the bottom of a body of water, by employing two outlets—one that floats and rises and falls with the water level in the tank and one that is fixed at the bottom or substantially lowest point of the tank—once more the objective of providing greater consistency in the density of the Zooplankton or other organism within the sample is achieved. Furthermore, an upper outlet tubing 66 in fluid communication with the upper outlet 58 and a lower outlet tubing 68 in fluid communication with the lower outlet 60 both are in fluid communication with a proportional flow valve 70 that further cooperates with the upper and lower outlets 58, 60 to regulate and normalize the flow of fluid from the main sample tank 52, the proportional flow valve 70 also mixing the fluid from the twin intakes 62, 64, again in the interest of yielding a relatively consistent sample density during the sampling event from the main sample tank 52. Downstream of the pre-conditioning section 30 there is operably positioned a second flow control 74 in fluid communication with the proportional flow valve 70 view tubing 72 that once again cooperates with other aspects of the system's control sub-system in moving the fluid therethrough and on to the microorganism stimulation section 80 and the rest of the microorganism evaluation system 20, as described further below. The flow control sub-system or any other devices such as pumps would effectively operate on a continuity principle aimed at providing a relatively clean, smooth, and consistent flow of fluid being sampled. Those skilled in the art will again appreciate that while an exemplary multiple-sample tank set-up is shown and described in connection with the exemplary microorganism evaluation system 20, each tank having respective inlets, outlets, vents, filters, and buoyant sample intakes and the fluid moved therethrough in cooperation with or under the control of one or more flow controls, the invention is not so limited, for example, as indicated, such sampling may instead involve a continuous real time monitoring scheme. Thus, any such sample collection, holding, and delivery hardware and related controls now known or later developed may be practiced in conjunction with the present invention without departing from its spirit and scope, such that the disclosed tank set-up is to be expressly understood as illustrative and non-limiting. More generally, the disclosed tank sub-system or other equivalent structure facilitates improved system performance through: (i) separation of live organisms from dead or inorganic material; (ii) removal of a significant amount of non-live material within the external sample tank 32 before entering the main sample tank 52 and rest of the microorganism evaluation system 20; (iii) lowering maintenance requirements due to reduced inorganic ingestion; (iv) mitigating the consequence of a relatively turbid water sample; and/or (v) providing a relatively less cluttered sample due again to the sample's relatively fewer dead or inorganic matter.

Regarding the microorganism stimulation section 80 within the microorganism evaluation system 20 that follows the tank sub-system or pre-conditioning section 30 above-described, and as further background, the general idea is that the microorganisms in the water being sampled/tested will physically respond to stimuli if they are alive and not if they are dead. This is, in fact, how it is done in the lab under a microscope, with the technician "poking" the organisms to see if movement can be observed. It is thus important to provide adequate stimulation of the microorganisms in a way that will cause a clearly detectable reaction by a living microbe; a microorganism that is alive will respond to the stimulation from this section 80 by generating its own movement, which self-generated movement is then isolated from the movement of the fluid sample in the flow normalizing section 100 and then detected in the viewing section 120, more about which is said below. It will also thus be further appreciated that the pre-sampling removal of dead or inorganic matter through settling or otherwise within the pre-conditioning section 30 again thereby contributes to the effectiveness of the downstream system, where the focus is to be on stimulating and detecting live microorganisms capable of motive response. But those skilled in the art will also appreciate that in some contexts the sample pre-conditioning section 30 will simply not be required, such as situations wherein the water sample has low turbidity or wherein the means of acquiring the sample, which of itself could be seen as another type of sample pre-conditioning device, is adequate to allow for meaningful downstream evaluation of organisms within the sample.

With continued reference to FIG. 2, then, in the first exemplary embodiment, an inertial disorientation section ("agitator") or microorganism stimulation section 80 is provided downstream of the sample pre-conditioning section 30 in order to subject the microorganisms to motive stimulation (agitator #1). Here, the stimulation section 80 is configured as a helix tube or disorientation spiral 82 having most likely more than one loop, though it will be appreciated that additional loops of various sizes and configurations can be added as required, any such geometries being dictated, at least in part, by the input determined for proper inertial stimulation of the microorganism. The theory is that the helix geometry of the disorientation spiral 82 will induce the fluid in the tube to rotate around the tubular axis, which will stimulate (agitate) the inertial sensing mechanisms found within the microorganisms, more about which is said below in connection with FIGS. 15 and 16.

Still in connection with FIG. 2, after the sample water leaves the microorganism stimulation section 80 wherein the flow is twisted and inertial effects are induced, it is then desirable to provide a flow normalizing section 100, or a section of the system conduit wherein the sample fluid has sufficient distance over which it is able to become relatively laminar, or wherein the radial or spiral flow is dampened out on its way to the viewing section 120. However, it will be appreciated that such dampening or relatively laminar flow may be achieved simply in the exit from the disorientation spiral 82 depending on its length and the diameter and surface features (smoothness or roughness) of the spiral bore 92 (FIG. 8) and/or in the viewing section body inlet 124 or viewing port 144 itself (FIGS. 3 and 4), such that in some embodiments the flow normalizing section 100 may not be employed. It will also be appreciated that such a normalizing section 100 may not be required at all or to the same extent in embodiments of the system wherein PSD direct or indirect hydraulic stimulation is employed, for example, such as in the alternative embodiments of FIGS. 17 and 18. Again, the primary purpose of the flow normalizing section 100 when it is employed is to effectively isolate self-generated movement of a microorganism from the movement of the fluid sample. In this way, once the fluid flow is returned to substantially "straight-line," any continued movement of a microorganism, as detected in the viewing section 120, would be deemed self-generated motion, as opposed to flow-generated motion. Thus, the normalizing inlet chute 102 (FIGS. 3, 5-7, 9 and 10) between the stimulation section 80 and the viewing section 120 of the microorganism evaluation system 20 is shown as being a relatively long, substantially linear chute that supports normalizing microorganism motion by providing a travel time that is less than the "disorientation response decay time" of the microorganisms, or the time from the reaction to the stimulation event beyond which an organism's induced response would be expected to cease, which for Zooplankton and other such organisms is thought to be on the order of 5-10 seconds. In other words, the normalizing chute 102 as in the exemplary embodiment is to be long enough to allow the flow to "straighten out" while not being so long that at the system's characteristic flow rate the disorientation response decay time for the microorganisms is exceeded by the time the fluid sample reaches the viewing section 120 from the stimulation section 80, such that self-generated movement of some kind would potentially not be seen in the viewing section 120 even for living or viable organisms. This "sizing" of the flow normalization section 100 and the inlet chute 102 particularly may be accomplished by utilization of CFD ("computational fluid dynamics") analysis to determine the length of the chute 102 required to normalize the motion of the microorganism before the viewing section 120, with one such exemplary inlet chute 102 geometry being shown and described below in connection with FIGS. 5-7, 9 and 10, though it will be appreciated by those skilled in the art that a number of other geometric variations and methods of their determination are possible depending on a variety of factors, again including the microorganism type and the fluid type. It will be additionally appreciated, as discussed further below, that the length of the normalizing chute 102, in the case of a substantially vertical arrangement of the flow normalizing section 100 as depicted schematically in FIG. 2, is the leading contributor to the overall column height of water within the system 20, or the change in height within the system 20 from the water level within the main sample tank 52 to the overall system exit or discharge point of sample return tube 200, which column height will not only have an influence on system flow rate but also create a pressure variance to which the microorganisms can respond as well.

Figures 3, 4:
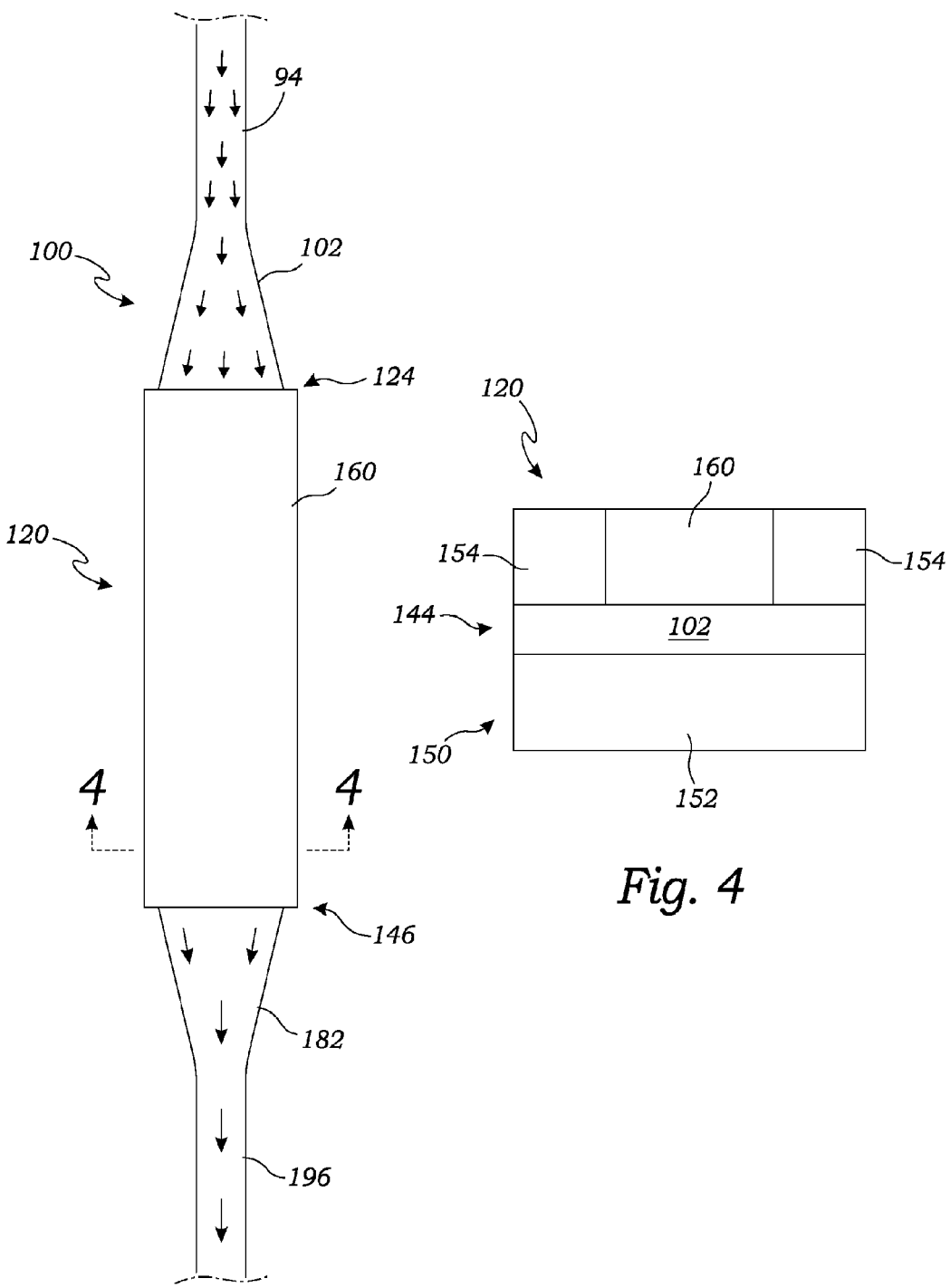
FIG. 3 is an enlarged partial schematic representation thereof taken along line 3-3 of FIG. 2, in accordance with at least one embodiment.
FIG. 4 is an enlarged partial schematic representation thereof taken along line 4-4 of FIG. 3, in accordance with at least one embodiment.

Turning next to the viewing section 120 shown schematically in FIG. 2, the fourth major hardware component or section of the microorganism evaluation system 20 according to aspects of the present invention, there are a number of features involving the physical, geometrical set-up alone that are specifically designed to accomplish the necessary data acquisition and are addressed in turn herein. The basic idea is that once the fluid sample has been pre-conditioned in the sample pre-conditioning section 30, the microorganisms within the sample have been stimulated in the stimulation section 80, and the flow within the system 20 regulated in the flow normalizing section 100, in the viewing section 120 visual data on the microorganisms is then obtained to support kinematics analysis and thereby determine whether any of the organisms are alive. First, as the flow enters the inlet chute 102 as schematically represented in FIG. 3, it basically flattens out and slows down through an expansion which causes a deceleration (negative acceleration or "−a"). The profile or cross-sectional area of the deceleration chute 102 is such to transition from the circular cross-section of the disorientation spiral 82 of the microorganism stimulation section 80 to a relatively larger rectangular cross-section of the viewing section 120, more about which is said below. The deceleration chute thus serves to reduce and normalize microorganism velocity through velocity change while not corrupting the self-induced relative motion of any organisms that are living. In fact, such deceleration or change in flow velocity is effectively another stimulus (agitator #2) to a living microorganism's sensory perception that would tend to induce further self-movement just before the organism enters the viewing section 120, even while the flow itself is slowing and further normalizing. Those skilled in the art will appreciate that such normalization is also desired, in part, in order to account for the relative difference in velocity across the profile as caused by the pipe walls, the flow and thus microorganism velocity at the center of any pipe being greater than at the walls where shear forces act on the fluid. The desirability of the flow or organism velocity slowing and normalizing prior to entering the actual viewing section 120 will be further appreciated upon consideration of the operation of the viewing section 120 itself.

In general, and with reference to FIGS. 2 and 3 and now FIG. 4, the viewing section 120 comprises a substantially flat or rectangular profile flow path through which optical equipment such as a digital camera "looks." It is contemplated that twenty (20) or more frames for each organism are desirable as a data set in order to draw conclusions about the organism's relative movement. It will thus be appreciated that obtaining the desired number of frames is essentially a function of the flow rate through the viewing section 120 and the optical equipment's imaging capabilities (optical system 160 and imager 170). Put another way, there are two primary aspects regarding the viewing section 120: (i) depth of field; and (ii) transit time—that is, through what cross-section can the optical equipment focus at a time, and how long is the segment of interest of the fluid within the viewer in order to get the snapshots for the data set. Accordingly, regarding the depth of field, the viewing section 120 preferably flattens out into a substantially rectangular profile defining the viewing port 144 of the viewing section 120 that is somewhat commensurate with the view angle or field of view of the optical system 160 (the camera or other optical sensor/equipment being used) and that has a depth that is within the focal length range of the optical system 160. Assuming currently available imaging components (lens field of view and focal lengths, resolution (on the order of twenty-four (24) megapixels), and full pixel array frame-rate), the aspects of the system of the present invention that dictate the function and performance of the viewing section 120 are primarily geometrical. For example, a camera capable of shooting at least ten (10) frames per second ("fps") at a processed "resolution" or image quality of at least 2 megapixels ("mp"), or a processed "1080P high definition video" as presently known, would be adequate for purposes of the present invention. Clearly, as technology advances are made, even faster or higher resolution digital cameras may be employed, which may then allow for higher sampling or flow rates and/or a smaller viewing section 120. More particularly, any such digital camera employed in the present invention may be characterized by a CCD (charge-coupled device)- and/or CMOS (complementary metal-oxide semiconductor)-based sensor or imager, though again it will be appreciated that any such digital imaging technology now known or later developed may be employed according to aspects of the present invention. Irrespective of the digital imaging technology employed, maintenance of relatively laminar or normalized flow and a proper microorganism velocity profile through the viewing section 120 so as to not compromise the data collected (relative movement detected is due to microorganism self-generation, not flow turbulence) is a related and overarching consideration of the present invention. Further regarding the viewing section 120, also integral to the assembly as shown in FIGS. 2-4 is an LED-based illuminator 150 or light source substantially adjacent to the viewing section 120, possibly opposite the optical system 150 as shown in FIG. 2. Or, as shown in FIG. 4, the illuminator 150 may comprise a background illuminator 152 opposite the optical system 160 and one or more front illuminators 154 adjacent the optical system 150, with further variations on the illuminator 150 shown and described in connection with FIG. 5 and following, further below. Not only does the illuminator 150 facilitate image acquisition by the imager 170 of the microorganisms within the fluid sample, but it will be appreciated that this "step change" in light provides yet another stimulus to the organisms themselves within the viewing section 120 itself (agitator #3), it being known in the art that such organisms often have photoreceptors or other capability of detecting and responding to light. Finally, to complete the viewing section 120, in the exemplary embodiment, the flow therethrough exits by way of a contraction or funnel of sorts, shown and described as an acceleration ("+a") chute or outlet chute 182. Much like the deceleration chute 102 at the inlet to the viewing section 120, the acceleration chute 182 profile or cross-sectional area is such to transition from the rectangular cross-section of the viewing section 120 to the relatively smaller circular cross-section of now the exit tubing 196. Downstream of the viewing section and the exit tubing 196 there is positioned effectively a third flow control 198 (flow control 46 and pressure/flow control 74 being upstream), which again cooperates with other aspects of the system's control sub-system in moving the fluid therethrough. Moreover, as mentioned above, there is effectively a column height of water within the system 20, or a difference in height within the system 20 from the water level within the main sample tank 52 to the overall system exit or discharge point effectively at the point of the third flow control 198, which column height creates a pressure variance that is yet another stimulus to which the microorganisms can respond (agitator #4). In more detail, Zooplankton in particular tends to generate vertical motion to adjust its depth, which is why higher concentrations of such organisms are typically found at or near the surface of a fluid versus deeper within the fluid. Therefore, such pressure differential or variance as is a natural byproduct of the physical set-up and spatial orientation of the exemplary microorganism evaluation system 20 as shown and described herein, which again serves as another stimulus or means of exciting self-generated motion in the microorganisms. It will thus be appreciated that as the fluid flows downwardly through the system, and particularly the inlet chute 102 of the flow normalizing section 100 on its way to the viewing section 120, living organisms will have a tendency to attempt to "swim upstream" seeking areas of relatively lower pressure. It would be an object of the system 20 to then detect any and all such motion by living microorganisms passing through the viewing section 120 so as to thereby evaluate or document organism effective viability within the test sample. Accordingly, and to further facilitate the control and use of such a pressure differential within the system, in the exemplary embodiment, the third flow control 198 is also configured with a pressure change or "ΔP" control that can be used to manipulate pressure within the system 20, and indirectly flow rate. Once more, those skilled in the art will appreciate that such structure and functionality may be substituted for by other technology now known or later developed without departing from the spirit and scope of the invention. For example, while a substantially vertical arrangement of the system 20 is shown and described in connection with the exemplary schematic of FIG. 2, it will be appreciated that such a spatial orientation or relationship among the components is merely illustrative. More particularly, while a "column height of water" has been discussed as one means of employing a change in pressure as another "agitator" or stimulation to an organism's senses within a fluid sample flowing through the system 20, it will be appreciated that pressure differential can be created in a variety of other ways employing pumps, valves, restrictions, and the like, or in some contexts such a "ΔP" agitator may be nominal if employed at all. In the exemplary embodiment, then, a pre-viewing section region, or deceleration or inlet chute 102, is configured as an expansion within the flow path to decelerate or slow the flow and hence the microorganisms to the desired viewing speed before reaching the primary viewing section 120 adjacent the imaging system. The portion of the viewing section 120 immediately beneath the optical system 160 (camera) is then effectively flattened such that from the side it may even be thinner than the conduit while from above it is relatively wider. The result again in the exemplary embodiment is a cross-sectional area within the viewing section 120 that is greater than that of the flow conduit, again contributing to a slower, relatively laminar flow and "normalized" motion of the organisms as they flow through this area, while also providing a thinner vertical section or "depth of field" for the viewing section 120, enabling the imaging system (optical system 160 and imager 170) to acquire visual data on the microorganisms at any depth within the flow as they pass through the viewing section 120. The width and depth of the viewing section 120 are thus dictated in large measure by the physical and optical properties of the camera or other imaging equipment employed. Current technology supports a dwell time in the viewing section 120 of on the order of one to five (1-5) seconds. As indicated, the dwell time can be manipulated by adjusting the flow rate of the system for example. Using an approximately twenty-four frames-per-second (~24 fps) digital video imager 170, this will potentially generate approximately twenty-four to one-hundred twenty (24-120) data frames. Therefore, those skilled in the art will appreciate that the entire system and approach is scalable by using various or even multiple lenses to acquire the desired visual data across the viewing section 120. As the flow leaves the viewing section 120, a post-viewing section region, or acceleration or outlet chute 182, is configured as a contraction within the flow path to accelerate or speed up the flow back to the system velocity after the viewing section 120. Once again, it will be appreciated by those skilled in the art that a variety of other such components and configurations are possible beyond those shown and described without departing from the spirit and scope of the invention.

It is further noted in connection with FIG. 2 that in the exemplary embodiment the overall size of the microorganism evaluation system 20 is on the order of 3 ft×2 ft×1.5 ft, clearly a portable size, such that the system 20 may advantageously be employed on ships and in other field uses. A relatively small package is also conducive to real time continuously monitoring applications in that the system 20 can be installed in relatively tight packaging constraints. Portability and simplicity of design are further accomplished by the use of gravitational, fluid dynamics effects as a means of flowing or circulating the sample fluid through the system 20 from the sample location to the exit point. In turn, such geometrical aspects of the design along with the conduit sizes create conditions whereby a determinant of system velocity is the height between the sampling location and the fluid exhaust point of the system, more about which is said below. However, again, there also may be some form of pump augmentation to facilitate system function, as required. It will be appreciated by those skilled in the art that other sizes and packages and related configurations of the system 20 are possible without departing from the spirit and scope of the invention, such that the above discussion is to be understood as merely illustrative.

With continued reference to FIGS. 1 and 2, image capture and processing hardware/software 210 is connected to the imager 170 through a relatively high bandwidth connection, or a connection sufficient for the data acquisition capability of the digital imager 170 employed; software on the image capture and processing device 210 operates to facilitate such image acquisition and manipulation. The data thus captured is then acted on by kinematics analysis software 212, whether residing on or within the same hardware as the image capture and processing device 210 or a different hardware or computing device. Such software 212 is configured to identify each microorganism as imaged by the viewing section 120 and essentially plot that organism's movement in a frame-by-frame or like fashion so as to thus determine relative angular (directional) or rotational motion or physiological change indicative of life, more about which is said below in connection with FIGS. 15 and 16. For example, the kinematics analysis software 212 might look at derivatives such as rate of change in path or rotation as indicative of self-induced motion by the organism and/or rate of change in aspect ratio alone or relative to the path (angular motion) or the organism's orientation (rotational motion) as indicative of self-induced body movement of the organism. It is contemplated that since again the standard velocity profile of the fluid flow in the system 20 will generate different velocities between organisms traveling at the center of a pipe and those that are traveling near the walls of the pipe, both the viewing section 120 and the motion detection software 212 are to be configured to account for such.

Figure 5:
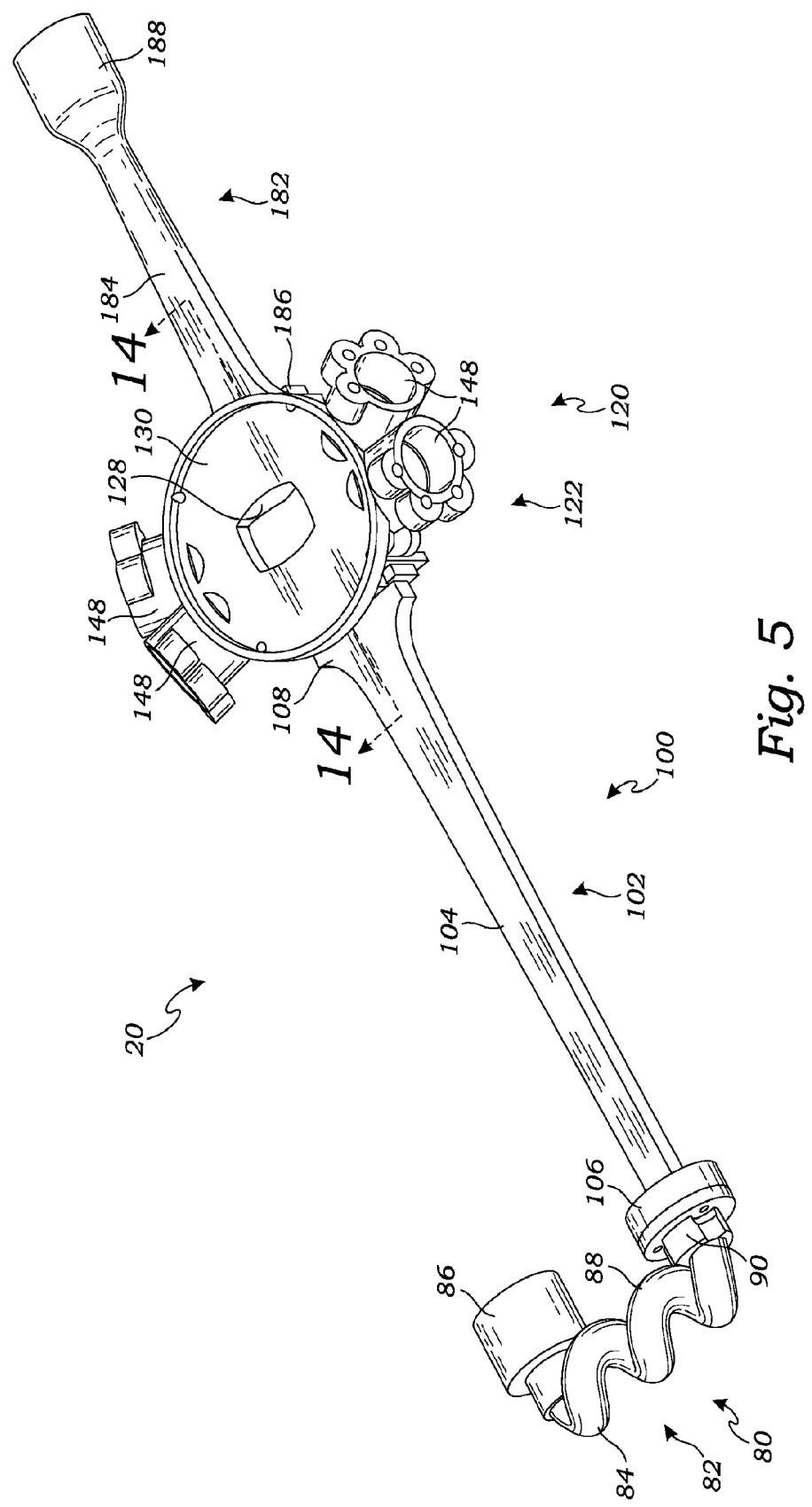
FIG. 5 is a partial perspective view thereof, in accordance with at least one embodiment.

Turning now to FIG. 5, there is shown a partial perspective view of an exemplary microorganism evaluation system 20 according to aspects of the present invention substantially consistent with the block diagram representation of FIG. 1 and the schematics of FIGS. 2-4. As a threshold matter, it is to be understood that the illustrated hardware components— here essentially the microorganism stimulation section 80, the flow normalizing section 100, and the viewing section 120, as well as the outlet chute 182 leading away from the viewing section 120—are merely representative or illustrative of aspects of the invention and are not limiting. In such views, it is noted that the pre-conditioning section 30 and other tubing, flow controls and the like are not shown for simplicity. Furthermore, the illuminator 150, the optical system 160, and the imager 170 are also not shown, though at least the illumination ports 148—four in the exemplary embodiment are shown wherein LEDs or the like may be installed so as to illuminate the interior cavity 126 of the viewing section 120, and the viewing port 144, specifically—are shown as being integral with the viewing section body 122. Regarding the optical system 160 and the imager 170, as explained above, these may be separate or integral components and "off the shelf" or proprietary, but in the exemplary embodiment a camera (not shown) is contemplated wherein the lens would mount or be removably installed directly to or on the optical system mount 130 of the viewing section body 122 such that the lens "looks" substantially straight into the cavity first opening 128 shown as intersecting the optical system mount 130 and, as best seen in the cross-sectional view of FIG. 14, communicating with the body cavity 126. Again, numerous other hardware components and configurations (geometry, means of assembly, etc.) are possible without departing from the spirit and scope of the present invention.

Figure 8:
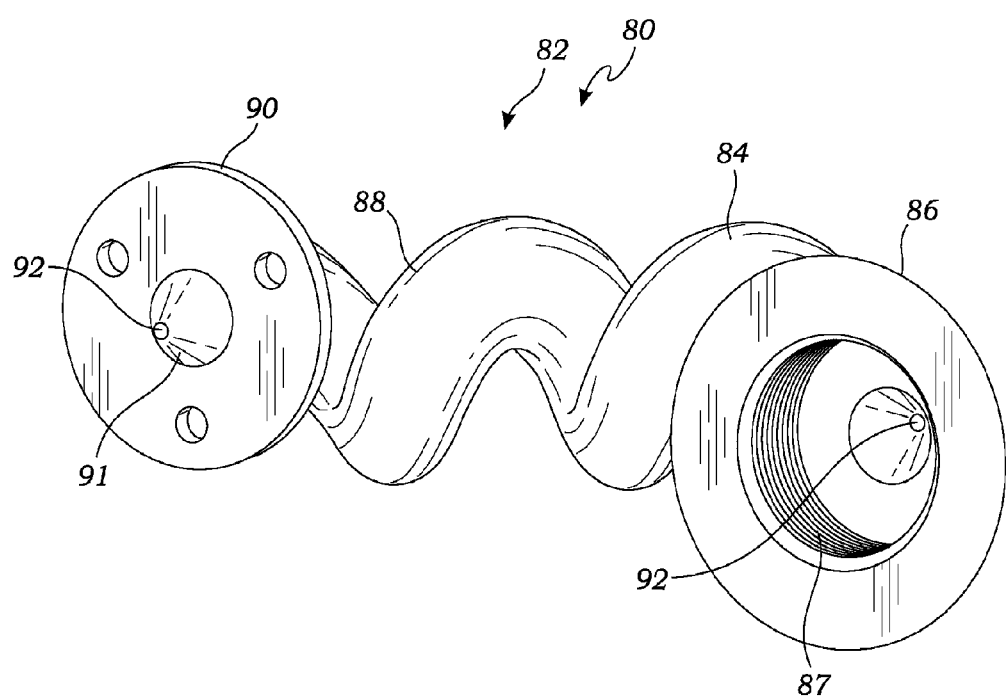
FIG. 8 is an enlarged partial perspective view thereof, in accordance with at least one embodiment.

With continued reference to FIG. 5, the microorganism stimulation section 80 is shown in the exemplary hardware embodiment as comprising a disorientation spiral 82 or helical tubular member. The disorientation spiral 82 is itself comprised of two turns—a first loop 84 and a second loop 88, each substantially comprising one revolution or a twist of three hundred sixty degrees 360°, though once again those skilled in the art will appreciate that any number and configurations of loops are possible within the scope of the invention, so long as sufficient rotation, twisting, or tumbling of the flow is provided so as to stimulate or excite the inertial sensing mechanisms of any living microorganisms within the sample flowing through the stimulation section 80. The first loop 84 is shown as having a proximal first loop coupling 86, which is configured for fluid connection to tubing 76 upstream of the stimulation section 80 through which the sample is delivered from the pre-conditioning section 30 (FIGS. 1 and 2). As best seen in FIG. 8, the first loop coupling 86 may be formed having an internally threaded bore 87 for threadably engaging an external thread on a mating coupling (not shown) formed on the end of the tubing 76, though it will be appreciated once more than any such coupling or removable engagement means now known or later developed may be employed. Similarly, the second loop 84 is formed having a distal second loop coupling 90 configured for fluid connection to the flow normalizing section 100 and specifically to an inlet chute first coupling 106. Here, as shown in FIG. 8, the second loop coupling 90 is formed as a conical fitting 91 configured to engage a conical bore 107 (FIG. 9) formed within the inlet chute first coupling 106 so as to open outwardly. As can also be seen in FIG. 8, there is formed axially or lengthwise along the entire disorientation spiral 82 a spiral inner bore 92 through which the sample flows. In the exemplary embodiment, the wall thickness of the disorientation spiral 82 (the first and second loops 84, 88) is approximately 3 mm and the inside diameter of the spiral bore 92 is approximately 1.2 mm, more about which will be said below in connection with the sizes of the other components of the exemplary system 20 and the operation thereof.

Figure 6:
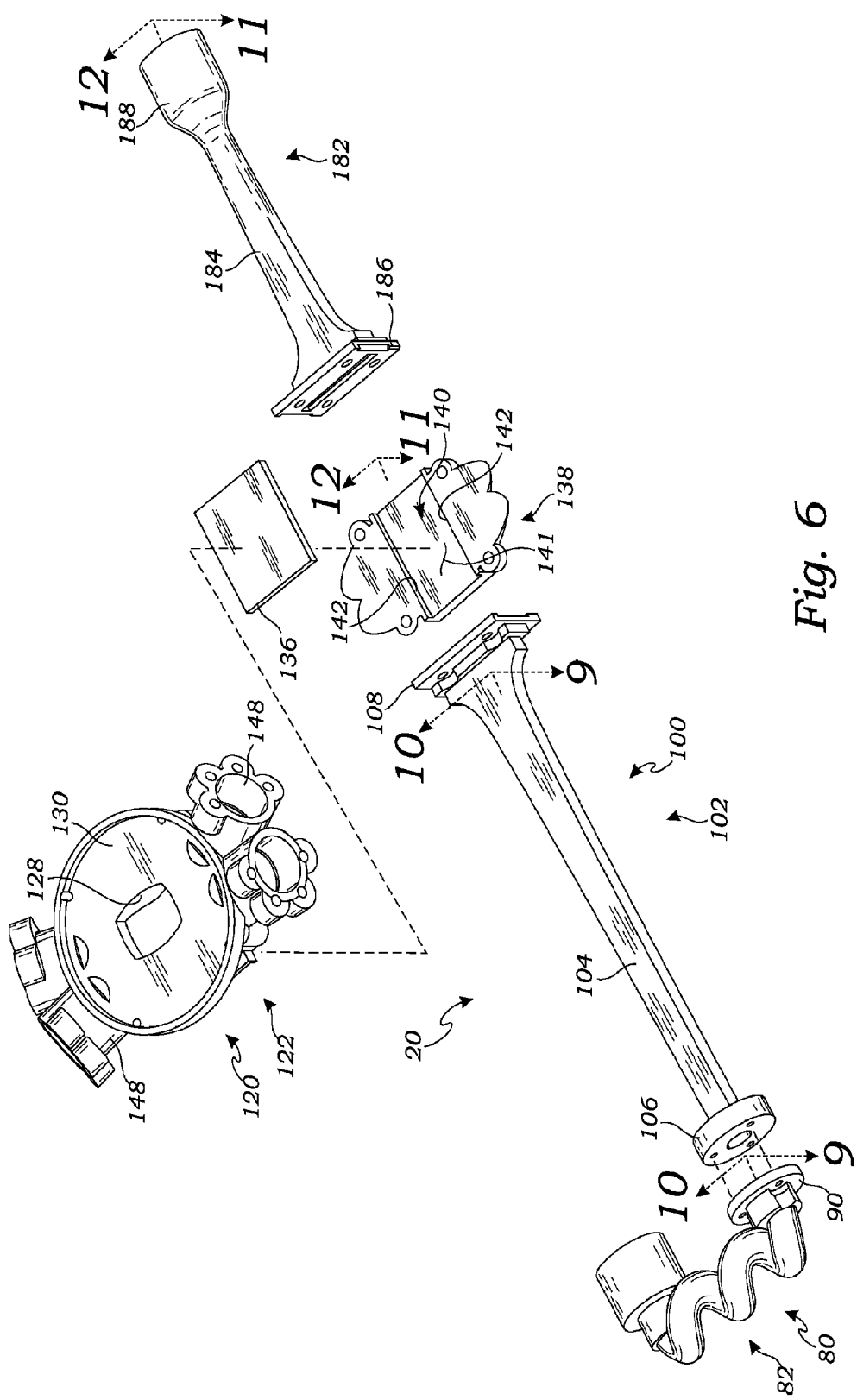
FIG. 6 is an exploded perspective view thereof, in accordance with at least one embodiment.
Figure 7:
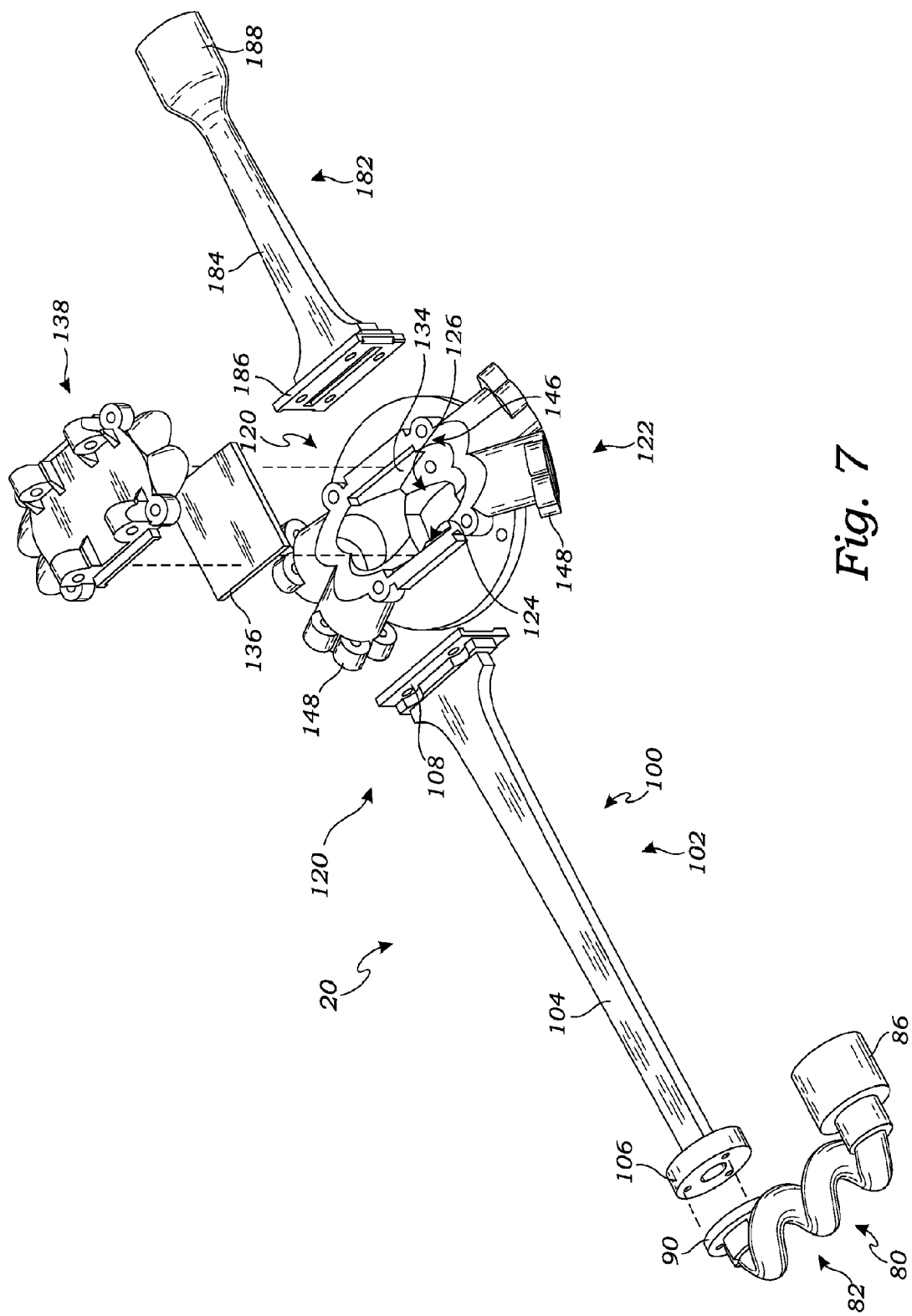
FIG. 7 is an exploded perspective view thereof taken from substantially the opposite direction as FIGS. 5 and 6, in accordance with at least one embodiment.
Figure 9:
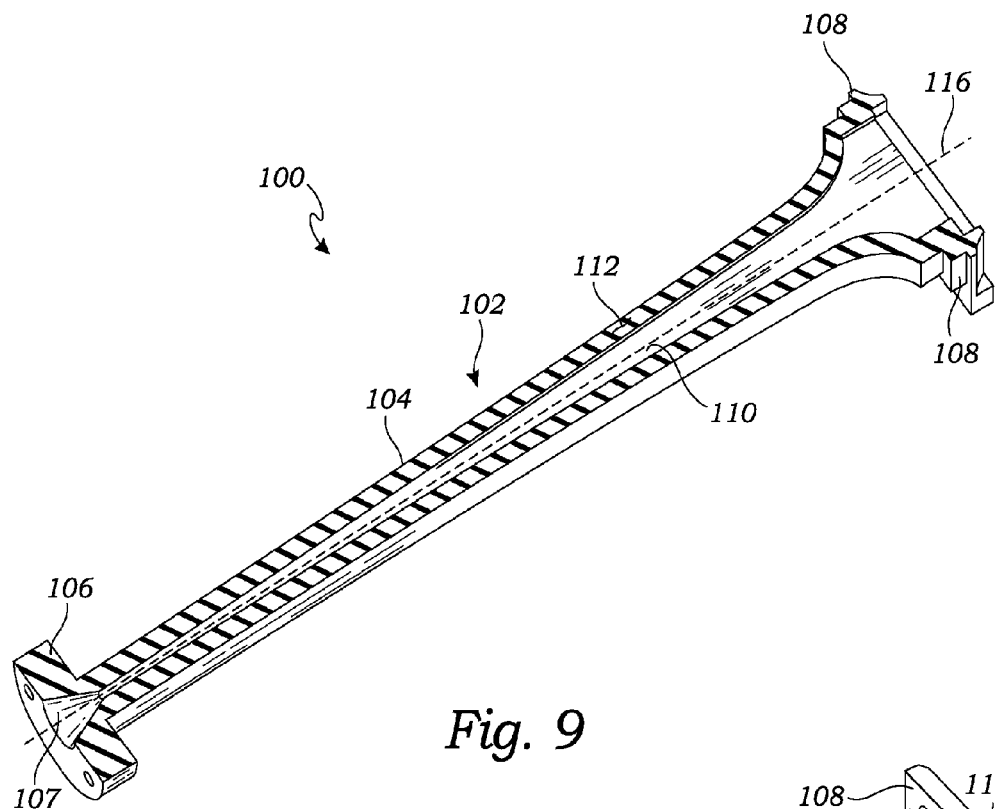
FIG. 9 is an enlarged partial top cross-sectional view thereof taken along line 9-9 of FIG. 6, in accordance with at least one embodiment.

Referring again to FIG. 5 and with further reference to the exploded perspective views of FIGS. 6 and 7, next in sequence is once again the flow normalizing section 100 that itself generally comprises the inlet chute 102. It is noted that while a section of tubing 94 is shown in FIG. 2 as interconnecting the stimulation section 80 and the flow normalizing section 100, in the embodiment shown in FIG. 5 and following, the system 20 instead has the disorientation spiral 82 connected directly to the inlet chute 102—it will be appreciated that any such connectivity of the respective parts of the system 20 is possible in the present invention without departing from its spirit and scope. The chute 102 again has at its proximal end the inlet chute first coupling 106 configured to connect to the spiral second loop coupling 90 and further has at its distal end an inlet chute second coupling 106 configured for connecting the inlet chute 102 to the viewing section body 122. Once more, though a particular form and geometry of the inlet chute second coupling 106 is shown, here in the form of plate substantially perpendicular to the axis 116 of the inlet chute 102 and having holes formed for the assembly thereof as by bolts or screws to the respective parts of the viewing section 120, the invention is not so limited. More notably, and now with further reference to the cross-sectional views shown in FIGS. 9 and 10, it can be seen that the exemplary inlet chute 102 has an inlet chute body 104 in which is formed an inlet chute inner bore 110 along its entire length. Taking first FIG. 9, a section taken through a substantially horizontal or inlet chute first plane 112, it can be seen that the bore 110 significantly tapers outwardly or expands from the entrance to the inlet chute 102 at the end adjacent the inlet chute first coupling 106 to the exit from the inlet chute 102 adjacent the inlet chute second coupling 108. In the exemplary embodiment, the proximal end of the inlet chute inner bore 110 immediately distal or downstream of the conical bore 107 defines an inlet chute first inside diameter that is substantially equivalent to the spiral inner bore 92 for a smooth transition therebetween. This substantially annular inner surface of the fluid flow path then gradually expands going down the inlet chute inner bore 110 to, in the exemplary embodiment, a final width of approximately 20 mm substantially corresponding to the width of the viewing port 144 within the viewing section 120, resulting in an expansion in this plane of about eight times (8×). Furthermore, referring to FIG. 10, a section taken through a substantially vertical or inlet chute second plane 114, or a plane substantially perpendicular to that along which the part is sectioned as shown in FIG. 9, the intersection of the inlet chute first and second planes 112, 114, in fact, being along or defining the inlet chute central axis 116, reveals that in this direction the inlet chute inner bore 110 is of a more uniform dimension. More particularly, at the entrance to the inlet chute 102 adjacent the inlet chute first coupling 106, the dimension across the bore 110 is again approximately 1.2 mm in the exemplary embodiment, which in this second plane 114 then actually tapers down slightly to approximately 1 mm to correspond to the depth of field D through the viewing section 120, more about which is said below. As such, the cross-sectional area of the flow path or inner bore 110 through the inlet chute 102 is approximately 1.1 mm² at its entrance ($\pi d^2/4 = \pi(1.2 \text{ mm})^2/4$) while at its exit it is approximately 20 mm² (20 mm×1 mm). It follows that there is a volumetric expansion along the inlet chute inner bore 110 of about twenty times (20×), and it will be appreciated, then, that as the sample flow passes from the disorientation spiral 82 into and through the inlet chute 102 it will have a tendency to normalize and slow down or decelerate as the flow path expands, resulting in relatively more laminar flow prior to the sample then leaving the inlet chute 102 or flow normalizing section 100 and entering the viewing section 120, a full appreciation of the benefit of which will be gained from the below discussion concerning the microorganism evaluation system 20 in use, and particularly FIGS. 16 and 17.

Figure 10:
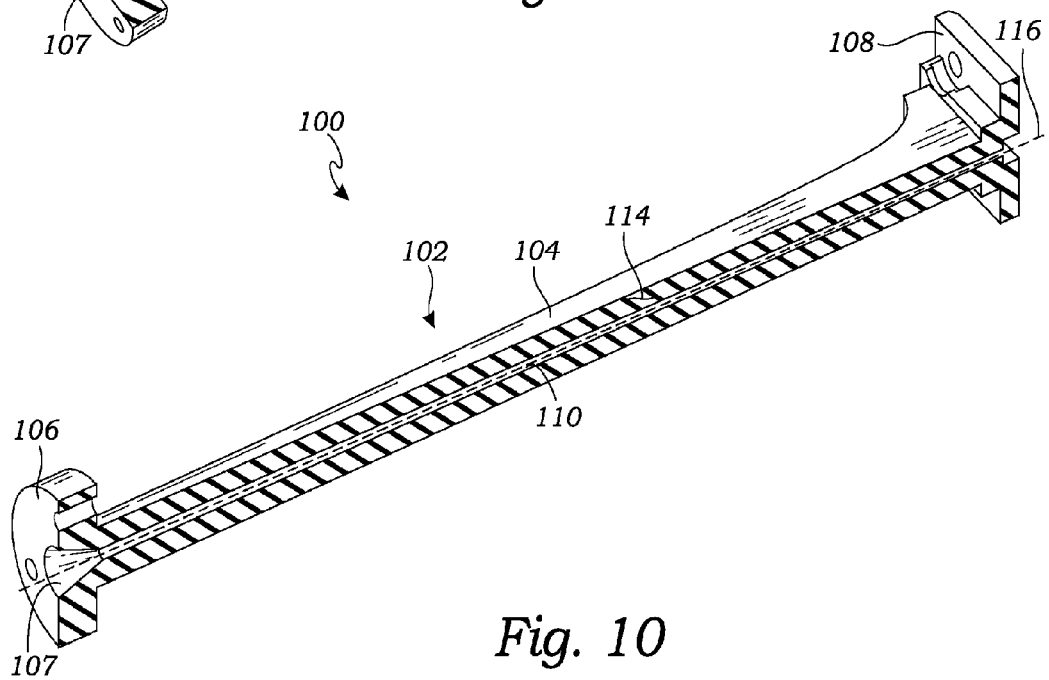
FIG. 10 is an enlarged partial side cross-sectional view thereof taken along line 10-10 of FIG. 6, in accordance with at least one embodiment.
Figure 11:
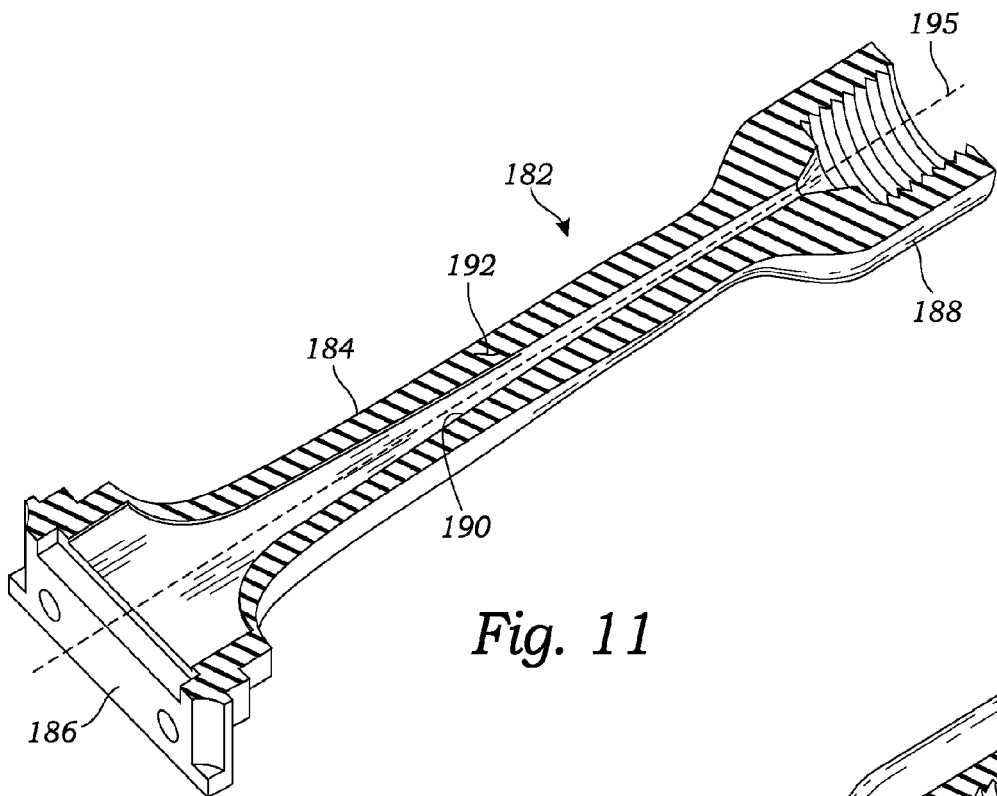
FIG. 11 is an enlarged partial top cross-sectional view thereof taken along line 11-11 of FIG. 6, in accordance with at least one embodiment.
Figure 12:
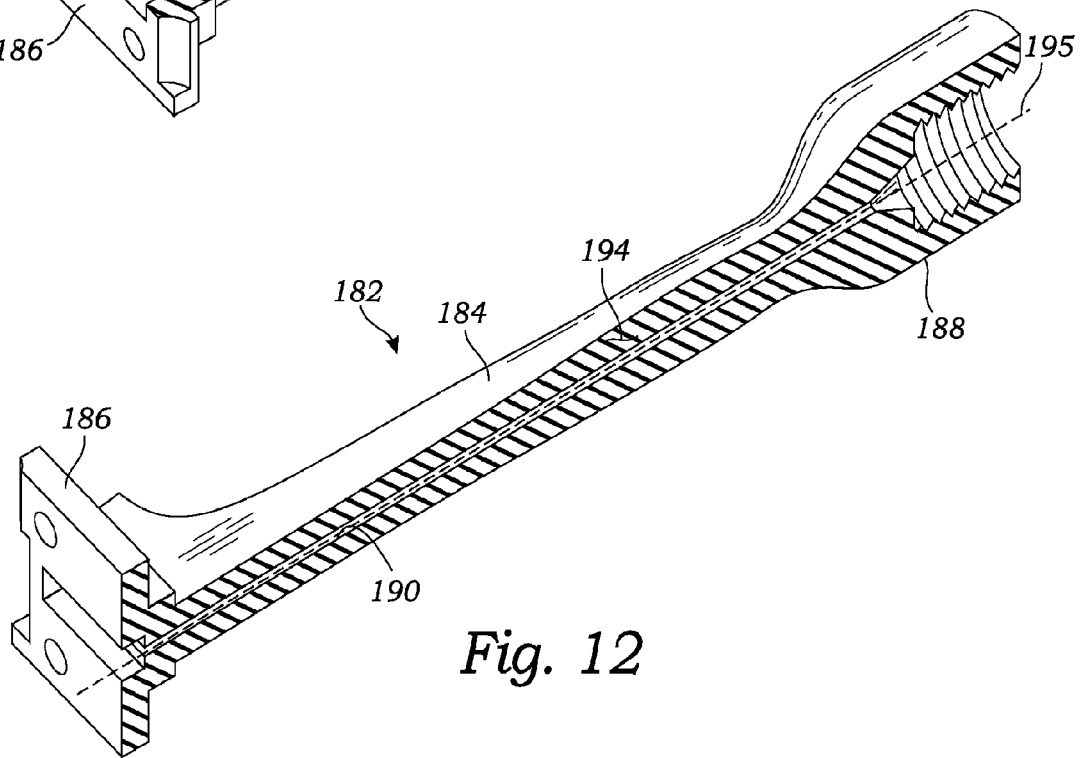
FIG. 12 is an enlarged partial side cross-sectional view thereof taken along line 12-12 of FIG. 6, in accordance with at least one embodiment.

Briefly turning to FIGS. 11 and 12, there are shown cross-sectional views of the outlet chute 182 analogous to the views of FIGS. 9 and 10 regarding the inlet chute 102, the outlet chute 182 effectively taking the sample flow away from the viewing section 100 (FIGS. 5-7) in much the same way, but in reverse, as the inlet chute 102 delivers the sample flow to the viewing section 120. Specifically, referring first FIG. 11 showing a section taken in or through a substantially horizontal or outlet chute first plane 192, it can be seen that the outlet chute inner bore 190 significantly tapers inwardly or contracts from the entrance to the outlet chute 182 at the end adjacent the outlet chute first coupling 186 that is connected to the viewing section body 122 to the exit from the outlet chute 182 adjacent the outlet chute second coupling 188 that is configured to connect to the tubing 196 (FIG. 2) leading eventually back out of the system 20. Whereas, as shown in FIG. 12, a section taken through a substantially vertical or inlet chute second plane 194, or a plane substantially perpendicular to that along which the part is sectioned as shown in FIG. 11, the intersection of the outlet chute first and second planes 192, 194, once again being along or defining the outlet chute central axis 195, reveals that in this direction the outlet chute inner bore 190 is of a more uniform dimension, here slightly expanding as the flow heads away from the viewing section 120 through the outlet chute 182. Once again, in reverse of the inlet chute 102, here with the outlet chute 182 there is an overall contraction or reduction in size of the inner bore 190 along its length in the direction of flow, which those skilled in the art will appreciate will have a tendency to gradually speed up again or accelerate the flow as it leaves the microorganism evaluation system 20. In the exemplary embodiment the inlet chute 102 is about twice as long as the outlet chute 182, or six inches (6 in) compared to three inches (3 in), respectively, though once more it will be appreciated that all such sizes and geometries are merely illustrative of features and aspects of the present invention and non-limiting.

Figure 13:
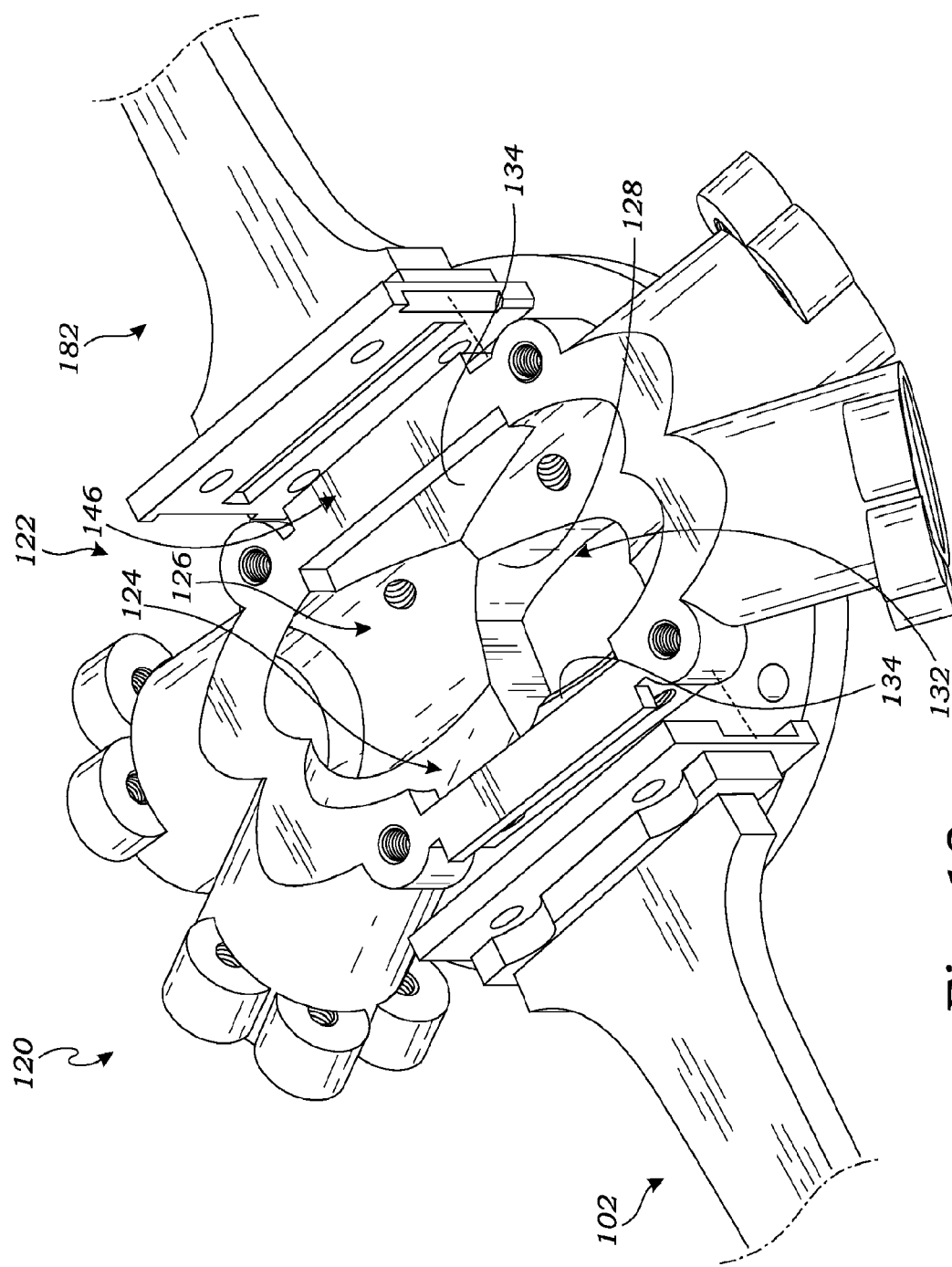
FIG. 13 is an enlarged partial bottom view thereof, in accordance with at least one embodiment.
Figure 14:
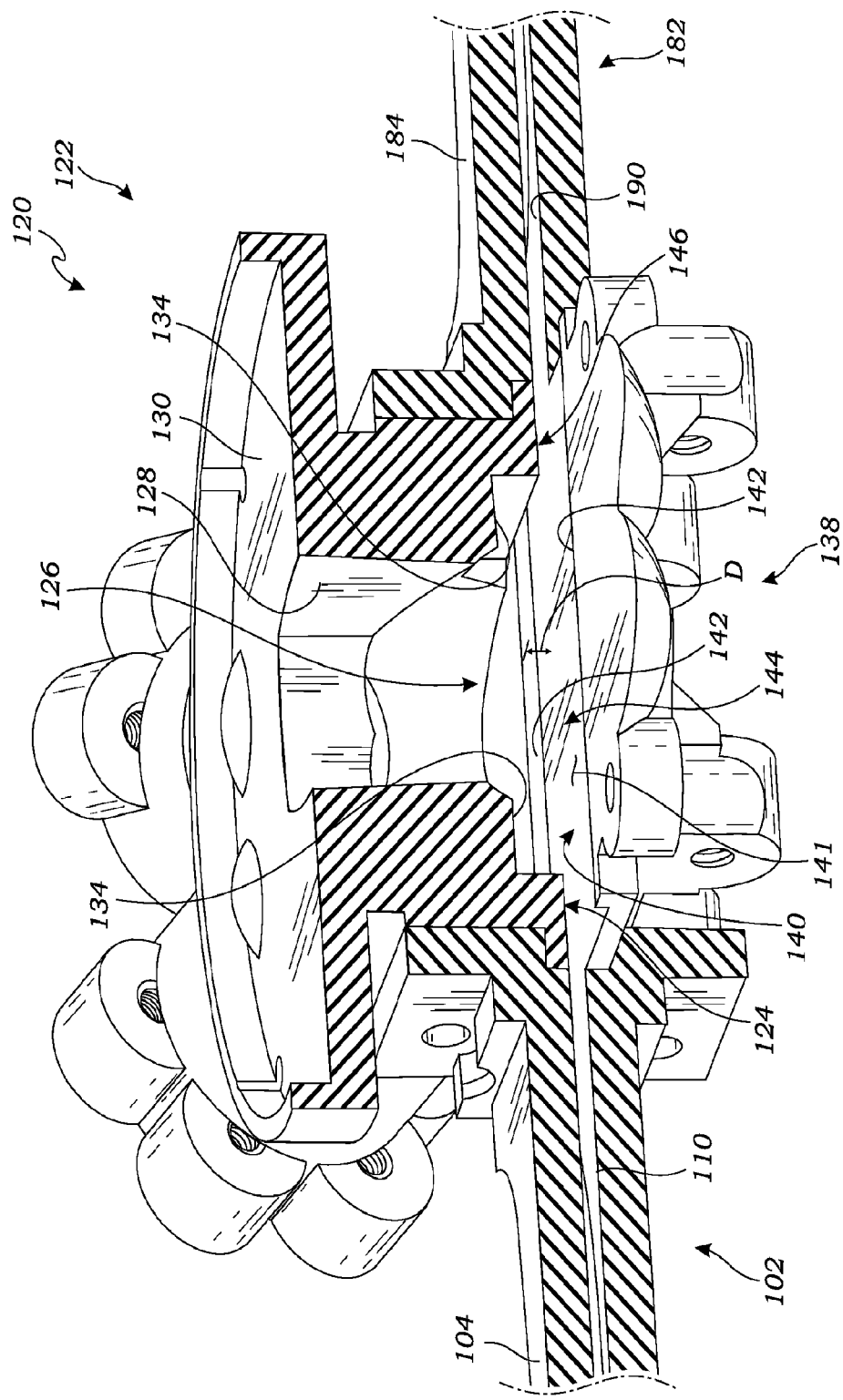
FIG. 14 is an enlarged partial cross-sectional view thereof taken along line 14-14 of FIG. 5, in accordance with at least one embodiment.

Referring again to FIGS. 5-7 and now with reference to FIGS. 13 and 14 as well, downstream of the flow normalizing section 100, or between the inlet and outlet chutes 102, 182, is again of course the viewing section 120. In the partial exploded view of FIG. 13, which is effectively the viewing section body 122 upside down with the back plate 138 not shown for clarity, it can be seen that in the exemplary embodiment the body 122 effectively has a viewing section body inlet 124 coinciding with the distal end of the inlet chute 102 at its second coupling 108 and a viewing section body outlet 146 coinciding with the proximal end of the outlet chute 182 at its first coupling 186, which inlet 124 and outlet 146 are each in fluid communication with the hollow interior of the viewing section 120, or the viewing section body cavity 126. In FIG. 14 there is shown a partial cross-sectional view of the viewing section 120, here with the viewing plate 136 not shown for clarity. As best appreciated from FIGS. 6 and 14, three sides of the actual viewing port 144 or the true flow path through the viewing section body cavity 126 are formed by a channel 140 formed in the back plate 138 that installs over the relatively larger cavity second opening 132 substantially opposite the cavity first opening 128 adjacent the viewing section optical system 160 as described above to substantially enclose the cavity 126, the back plate channel 140 having a channel bottom 141 and substantially perpendicular channel side walls 142. Opposite and substantially parallel to the channel bottom 141 there is positioned a clear or substantially transparent viewing plate 136 offset from the cavity first opening 128, the viewing plate 136 seating on opposite cavity shelves 134 formed in the viewing section body 122 so as to open into the cavity 126 and thus forming the fourth side of the viewing port 144. In the exemplary embodiment, the viewing plate 136 also seats on the tops of the channel side walls 142, or is pinched between the channel side walls 142 and the cavity shelves 134, such that it will be appreciated that the depth of the channel 140, or the height of the channel walls 142 effectively defines the height of the flow path through the viewing section 120 or the depth of field D for the optical system 160 that is "looking at" the sample flow through the cavity first opening 128, a portion of the open cavity 126, and the viewing plate 136 beneath which the flow is passing. It will be further appreciated that the dimensions of the viewing plate 136 substantially set the "footprint" size of the viewing port 144, which in the exemplary embodiment is 11.25 mm long by 20 mm wide, setting then a viewing port volume (L×W×H) of approximately 225 mm³ (11.25 mm×20 mm×1 mm). Again, this general geometry is discussed further below in terms of throughput and operation of the overall system 20, particularly in the context of FIGS. 16 and 17. With continued reference to FIGS. 5-7, 13 and 14, there is also shown multiple illumination ports 148 intersecting the viewing section body 122, in each of which there may be installed LEDs or the like so as to illuminate the interior cavity 126 of the viewing section 120, and the viewing port 144, specifically. Again, any number and configuration of such illumination ports 148 and any lighting units now known or later developed may be incorporated into the viewing section 120 without departing from the spirit and scope of the present invention.

Figure 15:
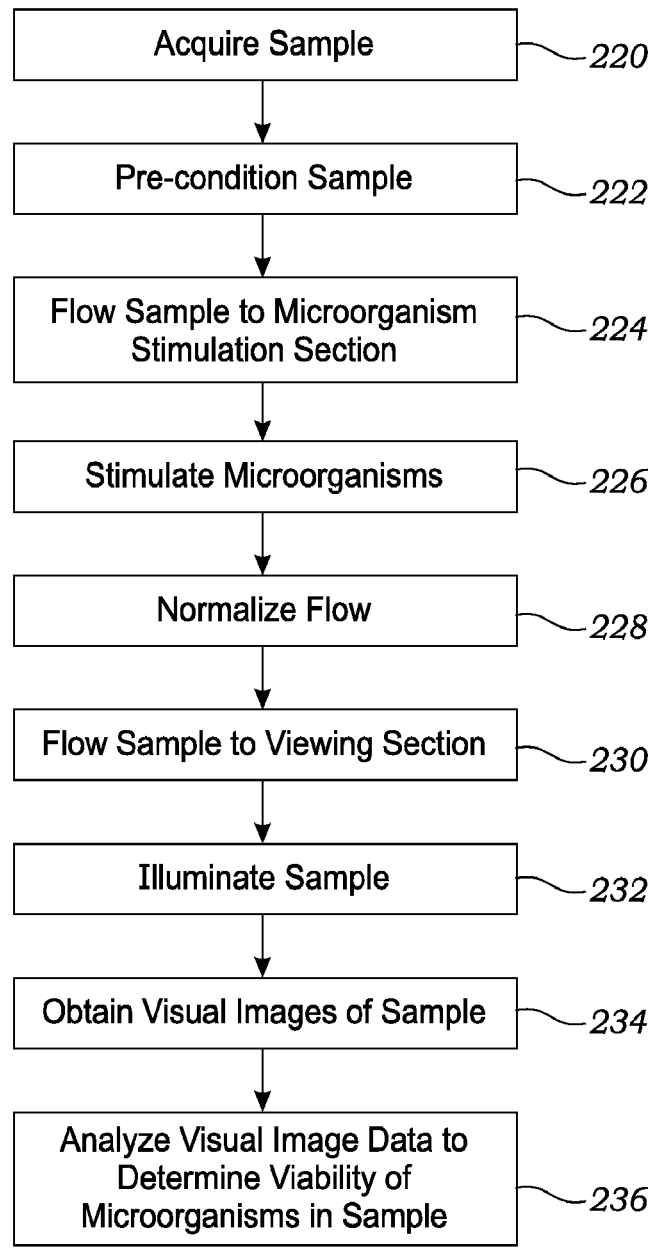
FIG. 15 is a flow chart representing the use thereof, in accordance with at least one embodiment.

Referring next to FIG. 15, there is shown a flow chart depicting the basic operation or use of a microorganism evaluation system 20 according to aspects of the present invention. In use of such an exemplary system 20 as shown in FIGS. 1-14, the first step 220 is to acquire the sample to be tested, which is beyond the scope of the present invention, though per the embodiment shown in FIGS. 1 and 2, there is one exemplary embodiment effectively a tank system identified here as the sample pre-conditioning section 30 made up of one or more tanks, here an external sample tank 32 and a main sample tank 52 (FIGS. 1 and 2), that together hold a finite volume of fluid sample for evaluation within or by the system 20. It will be appreciated that in other contexts different types and numbers of tanks may be employed, or a more continuous system may be employed wherein the fluid sample is acquired on a more real-time basis from a larger body or flow of water or other fluid. Once a sample is acquired, in step 222 the sample may be pre-conditioned, which stands for the general proposition of removing from the fluid sample inorganic or dead organic matter as by settling, filtration, or other appropriate techniques now known or later developed, so that what is primarily left in the water sample is organic material that may or may not be living, which determination is the primary purpose of the present invention. At step 224 the fluid sample is flowed to the microorganism stimulation section 80 (FIGS. 1 and 2), and at step 226 any microorganisms therein are stimulated, which again may be inertial stimulation as per the disorientation loop 82 shown in FIGS. 2 and 5, may be hydraulic or mechanical stimulation as shown and described below in connection with the alternative exemplary embodiments of FIGS. 18 and 19, or may be any other such stimulation device or method now known or later developed, any such device or method again stimulating or exciting the senses of the microorganisms, as compared with chemical staining or response and other such techniques known and employed in the art in determining organism life or viability, though in certain contexts such evaluation techniques (motive and chemical) may be used in tandem. At step 228, the flow is normalized as by flowing through the exemplary flow normalizing section 100 (FIGS. 1 and 2), and then at step 230 the sample passes into the viewing section 120 (FIGS. 1 and 2). At step 232 the sample within the viewing section 120 may be illuminated as by the illuminator 150 (FIGS. 1 and 2), and then the optical system 160 (FIGS. 1 and 2) in conjunction with the imager 170 (FIGS. 1 and 2) may obtain visual images of the sample at step 234. Finally, in terms of the general process or method of using the system 20, at step 236, the visual image data is analyzed to determine whether any of the microorganisms within the sample are living.

Figure 16A:
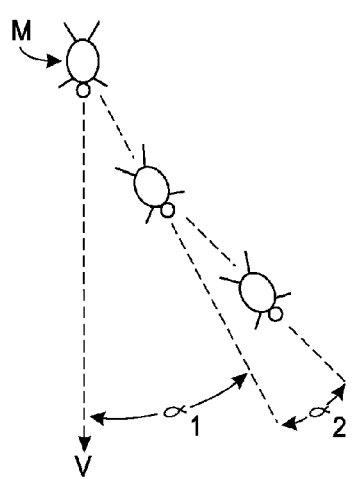
FIG. 16A is a schematic representation of a self-induced change in the direction of movement of a microorganism.
Figure 16B:
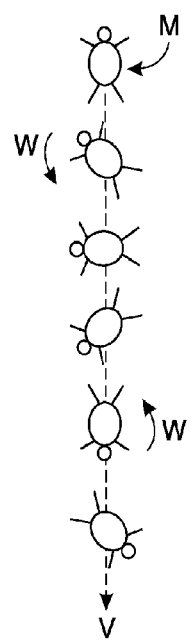
FIG. 16B is a schematic representation of a self-induced change in the orientation of a microorganism.
Figure 16C:
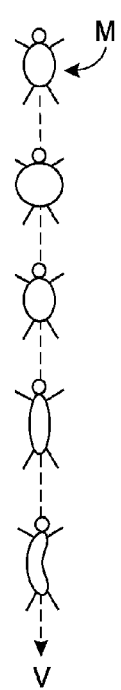
FIG. 16C is a schematic representation of a self-induced change in the aspect ratio of a microorganism.

In connection with this last step 236 (FIG. 15) and the analysis of the microorganisms of which image data is captured in the viewing section 120 after being excited in the stimulation section 80, referring now to FIGS. 16A-16C, there are shown schematics of essentially three different motive responses of a microorganism M that may be induced and thus be observed within the viewing section 120. The theory again is that the helix geometry of the disorientation spiral 82 (FIGS. 2 and 5) will induce the fluid in the tube to rotate around the tubular axis, which will stimulate (agitate) the inertial sensing mechanisms found within the microorganisms. A finite amount of time after the stimulation event has ended the living microorganisms will react with self-generated motion as their inertial measurement system stabilizes while they are floating in the "calm waters" of the viewing section 120. For example, they may attempt to straighten themselves out after they sensed being tumbled around. Another way of describing the thinking embodied in this aspect of the invention is that the microorganisms will react to "feeling dizzy." Accordingly, the microorganism stimulation section 80 shown in FIGS. 2 and 5 supports momentary stimulation of a live organism's inertial sensory perception. The amplitude and duration of stimulation necessary to induce such a response as self-generated motion, as by a "tumbling" microorganism attempting to "right" itself, can be characterized by both a frequency spectrum and a rotational time history. The frequency spectrum is particularly characterized by amplitude and frequency of the stimulation and can be expressed as power spectral density ("PSD"), whereas the rotational time history is particularly characterized by the rate and duration of the organism's motive response to the stimulation and can be expressed as energy spectral density ("ESD"), or the energy of the disorientation event. Certain microorganisms will be particularly sensitive to certain frequencies and amplitudes ("PSD"), which will be excited by an appropriate geometry of the spiral loop agitator or other such stimulus ("ESD"), as described above in connection with other aspects of the exemplary system of FIGS. 1-14 as well as in connection with the alternative embodiments shown particularly in FIGS. 18 and 19. Thus, the geometry or other properties of the helix are determined by the PSD, ESD, and acceleration profiles that are required to properly stimulate the microorganism M. In a bit more detail, again, the PSD describes both the frequency and amplitude of the stimulation event. Whereas, the ESD describes the time-history of the rotation profile of the stimulation event, such that the integral of this time-history, or "area under the curve," is the energy induced on the microorganism M during the stimulation event. Accordingly, the rotation profile depicts the "slopes" of the event, which is the rate of change of the rotational forces induced on the microorganism M. With a certain acceleration or rate-of-change in rotation being desirable, it being observed that microorganisms will adapt to relatively gentle motions and not necessarily generate counter-acting self-induced motion, while adequately rapid changes in the local hydrodynamic environment, or in acceleration or motion more generally, will tend to cause self-induced motion by the microorganism M. The optimal amount of stimulation required is bounded in both amplitude and duration, in that both parameters requiring a minimum threshold to be exceeded, and a maximum to not be attained. It will thus be appreciated once more that various geometries and features of the microorganism stimulation section 80 are possible beyond the double-loop spiral agitator 82 depicted in FIGS. 2 and 5, again depending on the type of organism that is to be evaluated, fluid type and flow characteristics, and other such contextual factors. Generally speaking, vertical orientations of the stimulation section 80 are preferred due the decoupling from localized pitching or roll motion (as on a boat for example), and the tendency of Zooplankton to generate a more vertical motion that supports a typical feeding pattern. Once more, then, those skilled in the art will appreciate that the invention is not limited to the particular stimulation section shown and described in connection with FIGS. 2 and 5, but may instead take a number of other forms to suit a particular context without departing from the spirit and scope of the invention. For example, in alternative embodiments, direct hydraulic excitation or indirect hydraulic (mechanical) excitation may be employed instead, such as by transverse water flows or vibration induction, as represented schematically in FIGS. 18 and 19. Any such approach would again employ a power spectral density ("PSD") generator to quantify the stimulation (amplitude and frequency of vibration or intensity/pressure and frequency of water pulses), more about which is said below. In connection with the "two loop" disorientation spiral 82 shown in FIGS. 2 and 5, such will tend to "saturate" the inertial sensing mechanism ("ISM") of the microorganism M so as to yield relatively more consistent results when the organism M is "released" from the spiral 82. In the exemplary embodiment, the geometry of the disorientation spiral 82 and the contemplated flows therethrough produce a rotational inertial stimulus of approximately six radians per second (6 rad/sec). After the flow normalization section 100 and entry of the sample into the viewing section 120 having in the exemplary embodiment a relatively high width-to-height aspect ratio, on the order of twenty to one (20:1), with the viewing chamber volume (L×W×H) again being 11.25 mm×20 mm×1 mm, it has been determined, for example, that utilizing current video camera technology with a nominal output resolution of 2.1 megapixels can resolve down to about ten (10) microns and will still allow for one to five second (1-5 sec) dwell times within the viewing port 144 and the acquisition of twenty (20) or more discrete frames per organism M—a sufficient and even substantial data set from which to make determinations regarding relative movement and hence organism life.

Referring first to FIG. 16A, then, there is shown schematically a microorganism M changing its direction incrementally by an angle α from the initial flow velocity vector v, indicating that it is living in deviating from the course or direction along which a non-living organism would be carried. This is one example of a motive response from a microorganism M that is essentially "swimming" in the "calm waters" of the viewing section 80 after having its ISM was saturated in the spiral stimulation section 80. As shown in FIG. 16B, another exemplary motive response is an organism M spinning as it travels along the normal flow velocity vector v, which again is not motion that would be induced by the laminar substantially straight-line flows through the viewing section 120, but would be indicative of self-generated motion by a living organism. And finally, as shown in FIG. 16C, yet another exemplary motive response that may be observed in a microorganism M that has been stimulated is a change in aspect-ratio, which essentially entails an organism twisting or wriggling or otherwise flexing or moving its body, any of which would again be self-generated and not a result of the sample flow, particularly within the viewing section 120. It will be appreciated that while discrete organism responses are shown in FIGS. 16A, 16B, and 16C, multiple such responses may be present in a single organism at the same time, such as an organism deviating from the normal flow velocity path and simultaneously rotating or spinning (combination of FIGS. 16A and 16B) or an organism maintaining the same flow velocity path but also wriggling and curling while rotating (combination of FIGS. 16B and 16C). Any combinations of such motive responses and others are possible, and the detection of one or more such movements as an organism passes through the viewing section 120 would be sufficient to indicate life.

Figure 17A:
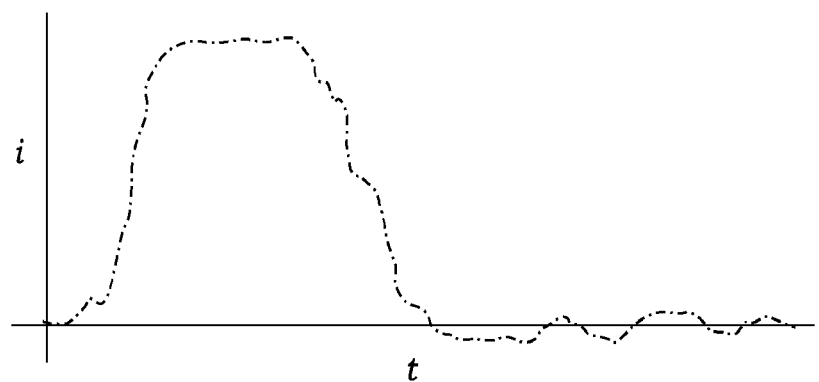
FIG. 17A is a graph depicting the inertial stimulation over time to which the microorganism is subjected, in accordance with at least one embodiment.
Figure 17B:
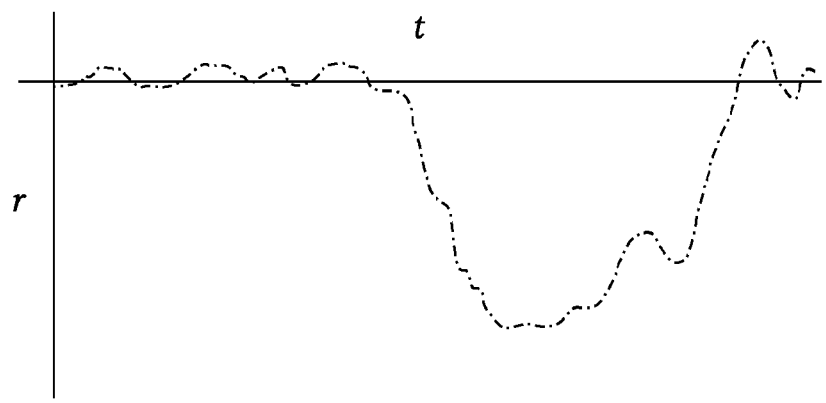
FIG. 17B is a graph depicting the response of a microorganism over time in response to the inertial stimulation depicted graphically in FIG. 17A, in accordance with at least one embodiment.

In terms of the organism image data aggregation and analysis—the detection and interpretation of microorganism motive response—attention is now directed to FIGS. 17A and 17B depicting the stimulation energy supplied to an organism and that organism's measured response, respectively. By way of further background, this portion of the discussion relating effectively both to the capabilities of the optical system 160 and imager 170 as well as the image capture and processing hardware/software 210 and the kinematics analysis algorithm 212, in addition of course to the geometry of the components and flow rates therethrough as described above, under certain conditions "artifacts" will be created by the digital imager 170, which will or could make quantitative interpretation incorrect. That is, there will be a certain level of inaccuracy in the amount of frame-to-frame apparent "motion" observed, depending on a number of factors. In a practical sense, when applying a derivative function it will tend to amplify any inaccuracies in spatial content, and therefore make more strict quantitate analysis problematic. However, there is relative robustness with the current approach regarding the identification of deviation from normal, not "how far" from normal; a qualitative analysis of the data—as in "Did the microorganism M move from the normalized path v?"—is an adequate determination in this context. Put another way, it is not necessary to know "how much" the microorganism M moved to know whether or not it is alive; detection of some movement (linear or rotational or of the aspect ratio, for example) from the normalized path or a starting orientation or body shape will qualitatively determine organism life, while still leaving open the option for quantitative assessment, including based on technological advances so as to reduce or eliminate the "artifacts" in the image data that could skew quantitative results. Technology in terms of optics (resolution) and processing (data transfer and compiling) is continuing to improve, so the artifacts that are generated will become less significant over time. And a very small percentage of the pixels will be changing from frame to frame in the present application, which will significantly reduce the amount of artifacts generated already. To further assist, the relatively small depth of field D (FIG. 4), in the exemplary embodiment on the order of one millimeter (1 mm), enables opening up the camera aperture and letting in more light for the image sensor 160, running greater practical shutter speed values, and producing greater clarity in the images captured.

Back to FIG. 17A, then, there is shown a graph depicting a representative inertial stimulation i (vertical axis) over time t (horizontal axis) to which the microorganism M is subjected. As can be seen, for a certain duration there is a definite inertial event, such as corresponding to the time the organism spends in the stimulation section 80, or the disorientation spiral 82, specifically, which energy then dampens out over time following discharge from the stimulation section 80, essentially corresponding to the time the organism spends in the flow normalizing section 100 and then the viewing section 120 where the flow rate of the fluid sample is slowest (the organism would have the longest "dwell time" in the "calm waters" of the viewing section). Then with reference to FIG. 17B, there is shown a similar graph now plotting a representative motive response r (vertical axis) over time t (horizontal axis), with the vertical axes of FIGS. 17A and 17B aligned so as to easily see the motive response r, as expected, time-wise lagging the inertial stimulation i. Moreover, the response r is plotted below the horizontal axis, or "negative," simply to indicate that the response r is in reaction to and "equal and opposite" or "proportional" to the inertial stimulation i. Notably, once again, it can be seen via a comparison of FIGS. 17A and 17B that it is not until after the inertial stimulation event has ended and the inertial stimulation i has begun to dampen out that the organism response r then sharply picks up, which period of active response again, based on the geometry and flow rates within the system 20, is to coincide with the time the organism is passing through the viewing section 120, which in the exemplary embodiment is to be approximately on the order of one to five (1-5) seconds. Those skilled in the art will appreciate that the graphs shown in FIGS. 17A and 17B, though based on actual observations, are not based on empirical data or the plotting of data points, and so in some sense are theoretical and so are not to be taken strictly or literally, hence there being no values or graduations on the graph axes. Accordingly, it will also be appreciated that various other scenarios of the inertial stimulation i and the motive response r are possible within the present invention without departing from its spirit and scope.

Turning now to FIG. 18, there is shown a schematic view of an alternative exemplary embodiment of a microorganism evaluation system 20 according to aspects of the present invention. Here, it is indicated that a hydraulic and/or mechanical excitation device 96 may be employed in or adjacent the flow some distance upstream of the viewing section 120, which agitator would again be coupled to a PSD generator 98. Generally, forces are hydraulically coupled to the organisms in the sample due to the fact that they are suspended in fluid. In direct hydraulic excitation or stimulation, a series of small tubes (not shown) intersecting the flow path may be employed to agitate the organisms as they pass through this excitation section 80, such as by a steady cross-flow or bursts or pulses of fluid transverse to the primary axis of fluid flow. Any such disruption, causing turbulence and tending to disorient the organisms, would thereby induce self-generated motion by living organisms in response, as discussed above. The concept of a reaction delay or an "agitation response decay time" wherein motion of the organisms is given time to commence but not too much time so as to commence and then cease before the viewing section 120, while still providing sufficient length in a normalizing section 100 or the like for the flow to normalize, as discussed above particularly in connection with FIG. 2, would again be applicable here in the context of hydraulic and/or mechanical excitation. With mechanical (indirect hydraulic) excitation, as in the system schematic of FIG. 19, the stimulus mechanism is effectively mechanical to hydraulic to inertial, such that this approach would be relatively less direct, as it is believed that ultimately the organisms respond to inertial stimuli. Either approach would again employ a power spectral density ("PSD") generator 96 to quantify the stimulation (amplitude and frequency of vibration in the context of mechanical excitation or intensity/pressure and/or frequency of water pulses in hydraulic excitation), and though the mechanical approach is shown in conjunction with stimulation at or contemporaneous with the viewing section 120 and the hydraulic approach upstream of the viewing section 120, other such variations are possible. Once more, it will be appreciated by those skilled in the art that while various embodiments and related operation have thus been shown and described, and particularly various means of exciting, agitating, or otherwise stimulating microorganisms, the invention is not so limited, but may instead involve any means now known or later developed for imparting at least inertial stimulation to organisms within a fluid flow for the purpose of determining whether any are living based on detected responsive movement and/or motion. Moreover, in some embodiments inertial stimulation may not even be employed, instead relying on some other agitator such as relative velocity, relative pressure, or light to stimulate the organisms in the test sample. Accordingly, it is to be expressly understood that features or aspects of the present invention as disclosed herein may be combined in various ways to achieve further alternate microorganism evaluation systems without departing from the spirit and scope of the invention.

Figure 20:
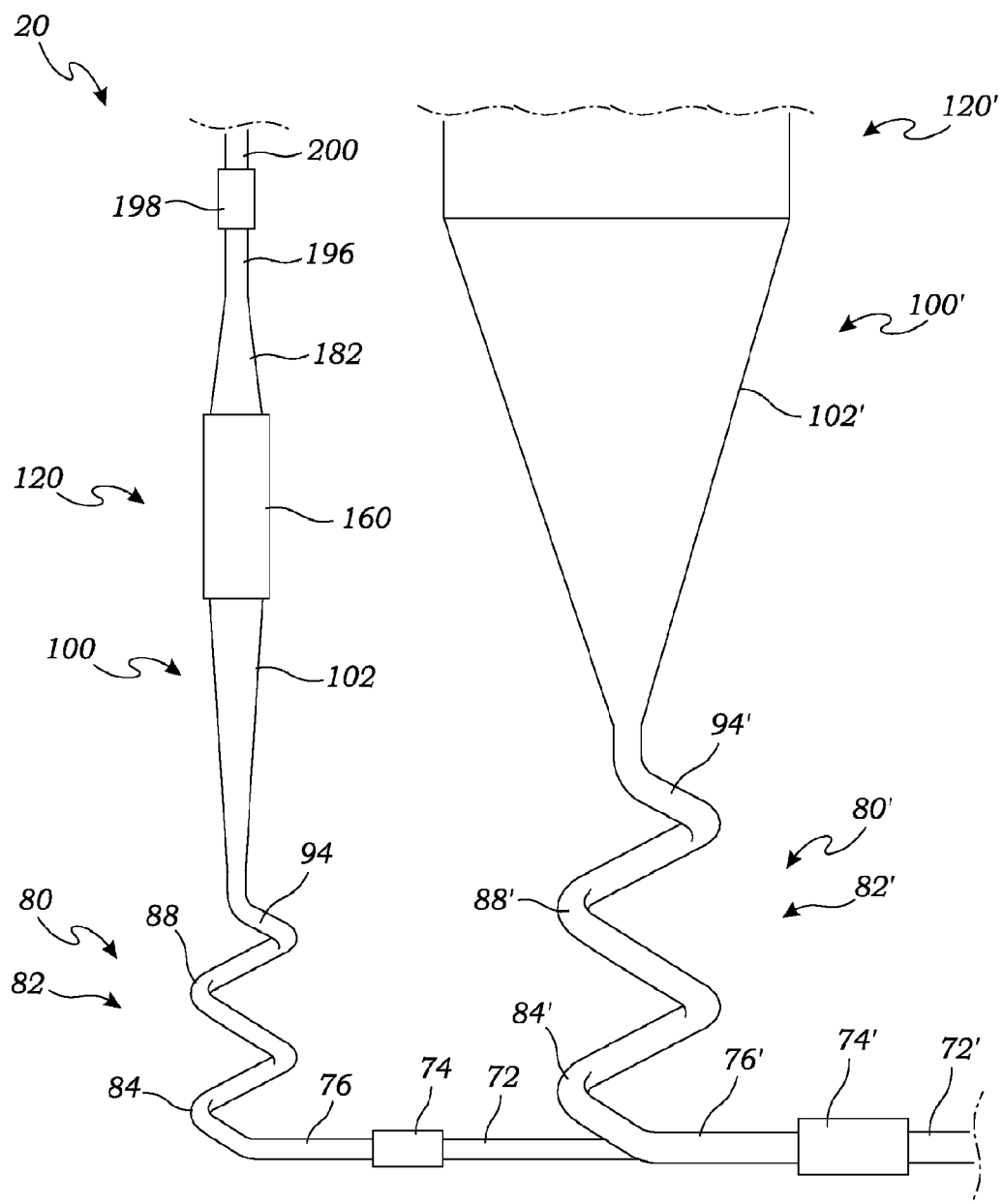
FIG. 20 is a partial schematic representation of a still further alternative exemplary microorganism evaluation system, in accordance with at least one embodiment.

Finally, in FIG. 20, there is shown an alternative dual microorganism evaluation system 20 having a first or primary, relatively larger microorganism stimulation section 80' that is otherwise quite analogous to that of the system 20 of FIGS. 1-14, which stimulation section 80' is itself sampled by a secondary microorganism stimulation section 80 that is in most respects the same as that of the first exemplary embodiment of FIGS. 1-14, such sampling being as by isokinetic sample, for example. For illustration, the larger disorientation spiral 82' may have an inside diameter of approximately 13 mm feeding into a viewing section 120' that is nominally 100 mm wide by 6 mm high, as compared to that of the first exemplary embodiment wherein the secondary spiral 82 in the dual system 20 of FIG. 20 has a nominal inside diameter of 1.2 mm and a viewing section 120 that is nominally 20 mm wide by 1 mm high. The resulting dual system 20 enables more throughput for use in contexts where larger volumetric or real-time sampling is desired as well as potentially enabling higher accuracy by secondary line sampling and evaluation within a viewing section 120 that has a nominal 1 mm depth of field while still allowing an acceptable aggregate throughput by employing the primary line having a nominal 6 mm depth of field, or a cross-sectional area of 600 $mm^2$ versus the 20 $mm^2$ of the secondary line that is more analogous to the exemplary embodiment system 20 according to aspects of the present invention. It will once again be appreciated that such features may be combined in a variety of ways and employ a variety of technologies now known or later developed without departing from the spirit and scope of the invention.

To summarize, regarding the exemplary embodiments of the present invention as shown and described herein, it will be appreciated that a microorganism evaluation system is disclosed and configured for imparting at least inertial stimulation to organisms within a fluid flow for the purpose of determining based on detected responsive movement and/or motion of the organisms whether any are living. Because the principles of the invention may be practiced in a number of configurations beyond those shown and described, it is to be understood that the invention is not in any way limited by the exemplary embodiments, but is generally directed to a microorganism evaluation system for analyzing microorganisms within a fluid flow, comprising a microorganism stimulation section and a viewing section in fluid communication therewith and having an optical system mounted relative to the viewing section body for viewing the fluid flow within the viewing port thereof, whereby image data relating to the fluid flow and any microorganisms therein is acquired via the optical system for analysis, and so is able to take numerous forms to do so without departing from the spirit and scope of the invention. It will also be appreciated by those skilled in the art that the present invention is not limited to the particular geometries and materials of construction disclosed, but may instead entail other functionally comparable structures or materials, now known or later developed, without departing from the spirit and scope of the invention. Furthermore, the various features of each of the above-described embodiments may be combined in any logical manner and are intended to be included within the scope of the present invention.

While aspects of the invention have been described with reference to at least one exemplary embodiment, it is to be clearly understood by those skilled in the art that the invention is not limited thereto. Rather, the scope of the invention is to be interpreted only in conjunction with the appended claims and it is made clear, here, that the inventor(s) believe that the claimed subject matter is the invention.

What is claimed is:

1. A microorganism evaluation system for analyzing microorganisms within a fluid flow, comprising:
   a microorganism stimulation section comprising a disorientation spiral having a spiral inner bore defining a first cross-sectional area and thereby allowing for a first flow rate therethrough of the fluid flow, the disorientation spiral configured for inducing a motive response in a living microorganism within the fluid flow passing therethrough; and
   a viewing section in fluid communication with the microorganism stimulation section, the viewing section comprising a body having formed therein a body cavity defining a viewing port visible through a cavity first opening formed in the body so as to be in communication with the body cavity, a viewing section body inlet and an opposite viewing section body outlet both being further formed in the body so as to be in communication with the body cavity and provide an unobstructed flow path therebetween through the viewing port, the viewing section further comprising an optical system mounted relative to the body for viewing the fluid flow within the viewing port through the cavity first opening, the optical system being a camera-like device capable of acquiring image data; further wherein:

the viewing section is configured in cooperation with the optical system such that multiple frames of image data relating to the fluid flow and a discrete microorganism therein are acquired via the optical system for analysis, movement of a microorganism relative to the fluid flow in response to flow through the disorientation spiral as per the acquired image data being indicative of microorganism viability; and wherein:

the viewing port of the viewing section defines a second cross-sectional area, the second cross-sectional area being greater than the first cross-sectional area and thereby causing a second flow rate therethrough of the fluid flow to be less than the first flow rate, whereby the fluid flow through the viewing port is rendered relatively slow and laminar, thereby contributing to acquisition of the multiple frames of image data.

2. The system of claim 1 further comprising a hydraulic/mechanical excitation device.

3. The system of claim 2 wherein the hydraulic/mechanical excitation device is upstream of the viewing section.

4. The system of claim 2 wherein the hydraulic/mechanical excitation device is co-located with the viewing section.

5. The system of claim 1 further comprising a flow normalizing section in fluid communication between the microorganism stimulation section and the viewing section, the flow normalizing section comprising an inlet chute having a tapered inlet chute inner bore.

6. The system of claim 5 wherein:
the inlet chute is formed with an inlet chute first coupling configured for connecting to the microorganism stimulation section, the inlet chute inner bore also defining at the inlet chute first coupling the first cross-sectional area of the spiral inner bore of the disorientation spiral and thereby allowing for the first flow rate therethrough of the fluid flow; and
the inlet chute is further formed with an inlet chute second coupling configured for connecting to the viewing section and also defining at the inlet chute second coupling the second cross-sectional area of the viewing port and thereby allowing for the second flow rate therethrough of the fluid flow, whereby the inlet chute of the flow normalizing section receives the fluid flow at the first flow rate as delivered by the disorientation spiral of the microorganism stimulation section and delivers the fluid flow at the second flow rate to the viewing port of the viewing section.

7. The system of claim 5 wherein:
the inlet chute is formed in an inlet chute first plane and a perpendicular inlet chute second plane, the inlet chute first and second planes intersecting along an inlet chute central axis; and
the inlet chute inner bore is tapered in the inlet chute first plane greater than in the inlet chute second plane, whereby the inlet chute inner bore in the inlet chute second plane is substantially equivalent to the spiral inner bore.

8. The system of claim 7 wherein the viewing port of the viewing section defines a depth of field in the axis of the cavity first opening that is substantially equivalent to both the spiral inner bore and to the inlet chute inner bore in the inlet chute second plane.

9. The system of claim 1 wherein the viewing section further comprises an illuminator.

10. The system of claim 9 wherein:
the body is formed having at least one illumination port substantially communicating with the body cavity, the at least one illumination port being offset from the cavity first opening; and
the illuminator comprises an at least one light source positioned within the at least one illumination port.

11. The system of claim 1 further comprising a sample pre-conditioning section upstream of and in fluid communication with the microorganism stimulation section.

12. The system of claim 11 wherein the sample pre-conditioning section comprises:
an external sample tank; and
a main sample tank in fluid communication with the external sample tank and with the microorganism stimulation section.

13. The system of claim 1 wherein a primary microorganism stimulation section and viewing section are configured so as to be sampled by a secondary microorganism stimulation section and viewing section, the primary microorganism stimulation section being at least double the size of the secondary microorganism stimulation section and the primary viewing section being on the order of five times the width and thirty times the cross-sectional area of the secondary viewing section.

14. The system of claim 1 wherein the fluid flow within the viewing port of the viewing section defines a transit time for each microorganism within the fluid flow of at least one second, the transit time being the amount of time each microorganism dwells within the viewing port so as to be visible to the optical system, whereby the transit time contributes to the acquisition of the multiple frames of image data.

15. The system of claim 1 wherein at least ten frames of image data are acquired for each microorganism.

16. A microorganism evaluation system for analyzing microorganisms within a fluid flow, comprising:
a means for inducing a motive response in a living microorganism within the fluid flow;
a flow normalizing section comprising an inlet chute having a tapered inlet chute inner bore; and
a viewing section in fluid communication with and downstream of the flow normalizing section, the viewing section comprising a body having formed therein a body cavity defining a viewing port visible through a cavity first opening formed in the body so as to be in communication with the body cavity, a viewing section body inlet and an opposite viewing section body outlet both being further formed in the body so as to be in communication with the body cavity and provide an unobstructed flow path therebetween through the viewing port, the viewing section further comprising an optical system mounted relative to the body for viewing the fluid flow within the viewing port through the cavity first opening; further wherein:
the viewing section is configured in cooperation with the flow normalizing section and the optical system such that multiple frames of image data relating to the fluid flow and a discrete microorganism therein are acquired via the optical system for analysis, movement of a microorganism in response to the means for inducing as detected in the viewing section being indicative of microorganism viability.

17. The system of claim 16 wherein the means for inducing comprises at least one of a disorientation spiral and a hydraulic/mechanical excitation device co-located with a microorganism stimulation section in fluid communication with and upstream of the flow normalizing section.

18. The system of claim 16 wherein the means for inducing comprises the inlet chute co-located with the flow normalizing section.

19. The system of claim 16 wherein the means for inducing comprises at least one of a light source and a hydraulic/mechanical excitation device co-located with the viewing section.

20. The system of claim 16 wherein:
the inlet chute is formed with an inlet chute first coupling defining a first cross-sectional area of the inlet chute inner bore and thereby allowing for a first flow rate therethrough of the fluid flow; and
the inlet chute is further formed with an inlet chute second coupling configured for connecting to the viewing section and defining a second cross-sectional area of the inlet chute inner bore, the second cross-sectional area being greater than the first cross-sectional area and thereby causing a second flow rate therethrough of the fluid flow to be less than the first flow rate.

21. The system of claim 20 wherein:
the means for inducing further comprises a disorientation spiral having a spiral inner bore further substantially defining the first cross-sectional area; and
the viewing port further substantially defines the second cross-sectional area, whereby the inlet chute of the flow normalizing section receives the fluid flow at the first flow rate as delivered by the disorientation spiral and delivers the fluid flow at the second flow rate to the viewing section.

22. The system of claim 16 wherein:
the inlet chute is formed in an inlet chute first plane and a perpendicular inlet chute second plane, the inlet chute first and second planes intersecting along an inlet chute central axis;
the inlet chute inner bore is tapered in the inlet chute first plane greater than in the inlet chute second plane; and
the viewing port of the viewing section defines a depth of field in the axis of the cavity first opening that is substantially equivalent to the inlet chute inner bore in the inlet chute second plane.

23. A microorganism evaluation system for analyzing microorganisms within a fluid flow, comprising:
a sample pre-conditioning section;
a microorganism stimulation section in fluid communication with the sample pre-conditioning section, the microorganism stimulation section comprising a disorientation spiral for inducing a motive response in a living microorganism within the fluid flow passing through the disorientation spiral;
a flow normalizing section in fluid communication with the microorganism stimulation section, the flow normalizing section comprising an inlet chute having a tapered inlet chute inner bore; and
a viewing section in fluid communication with the flow normalizing section, the viewing section comprising a body having formed therein a body cavity defining a viewing port visible through a cavity first opening formed in the body so as to be in communication with the body cavity, a viewing section body inlet and an opposite viewing section body outlet both being further formed in the body so as to be in communication with the body cavity and provide an unobstructed flow path therebetween through the viewing port, the viewing section further comprising an optical system mounted relative to the body for viewing the fluid flow within the viewing port through the cavity first opening; further wherein:
the viewing section is configured in cooperation with the flow normalizing section and the optical system such that at least ten frames of image data relating to the fluid flow and a discrete microorganism therein are acquired via the optical system for analysis, movement of a microorganism in response to passing through the disorientation spiral as detected in the viewing section being indicative of microorganism viability.

\* \* \* \* \*